US012788582B2

(12) United States Patent
Betz et al.

(10) Patent No.: US 12,788,582 B2
(45) Date of Patent: Nov. 10, 2026

(54) IMPLANT SYSTEMS AND METHODS FOR STABILIZING A BONE FROM AN ANTERIOR APPROACH

(71) Applicant: Foundation Surgical Group, Inc., Scottsdale, AZ (US)

(72) Inventors: Randal R. Betz, Bradenton, FL (US); Michael Sherman, Memphis, TN (US); Charlie Barfield, Nesbit, MS (US); Dimitri K. Protopsaltis, Memphis, TN (US); Asher Breverman, Scottsdale, AZ (US); Christopher Reah, Taunton (GB)

(73) Assignee: FOUNDATION SURGICAL GROUP, INC., Scottsdale, AZ (US)

( * ) Notice: Subject to any disclaimer, the term of this patent is extended or adjusted under 35 U.S.C. 154(b) by 0 days.

(21) Appl. No.: 19/322,647

(22) Filed: Sep. 8, 2025

(65) Prior Publication Data

US 2026/0069429 A1 Mar. 12, 2026

Related U.S. Application Data

(63) Continuation-in-part of application No. PCT/US2025/045274, filed on Sep. 7, 2025, and a (Continued)

(51) Int. Cl.
*A61F 2/44* (2006.01)
*A61B 17/064* (2006.01)

(Continued)

(52) U.S. Cl.
CPC .......... *A61F 2/447* (2013.01); *A61B 17/0642* (2013.01); *A61B 17/56* (2013.01);

(Continued)

(58) Field of Classification Search
CPC ...... A61F 2/4455; A61F 2/446; A61F 2/4465; A61F 2/447; A61F 2/30749;

(Continued)

(56) References Cited

U.S. PATENT DOCUMENTS

| | | |
|---|---|---|
| 583,455 A | 6/1897 | Bush |
| 4,047,524 A | 9/1977 | Hall |

(Continued)

FOREIGN PATENT DOCUMENTS

| | | |
|---|---|---|
| AT | E119015 T1 | 3/1995 |
| AU | 3965489 A | 1/1990 |

(Continued)

OTHER PUBLICATIONS

Kamikawa, Tracy L., Non-Final Office Action for U.S. Appl. No. 18/347,655, Mailed Nov. 3, 32025, 36 pgs., United States Patent and Trademark Office, Alexandria, VA , USA.

(Continued)

*Primary Examiner* — Ellen C Hammond
(74) *Attorney, Agent, or Firm* — John Brooks Law LLC; John J. Brooks, III

(57) ABSTRACT

An implant system comprising one or more staple and a cage is disclosed. The implant system is secured to a bone by moving the staple whereby tines of the staple frictionally and mechanically engage or embed themselves in the bone sidewalls. In some embodiments, the staple comprises a first staple and a second staple. In some embodiments, the staples are positioned transverse to an approach trajectory of positioning of the implant system. The implant system may be configured for use as an interbody or intrabody implant system. The implant system may further comprise tools for positioning the implant system. Some embodiments of the implant device are configured to be positioned from an anterior trajectory, an anterior lateral approach trajectory, or (Continued)

an anterior oblique approach trajectory relative to the bone. Some embodiments of the implant device are configured to be used in an anterior lumbar interbody fusion (ALIF) procedure.

32 Claims, 17 Drawing Sheets

Related U.S. Application Data continuation-in-part of application No. PCT/US2025/045275, filed on Sep. 7, 2025.

(60) Provisional application No. 63/692,618, filed on Sep. 9, 2024, provisional application No. 63/692,693, filed on Sep. 9, 2024.

(51) Int. Cl.
*A61B 17/56* (2006.01)
*A61F 2/30* (2006.01)

(52) U.S. Cl.
CPC ...... *A61F 2/30749* (2013.01); *A61F 2/30771* (2013.01); *A61B 2017/564* (2013.01); *A61F 2002/30261* (2013.01); *A61F 2002/30367* (2013.01); *A61F 2002/30372* (2013.01); *A61F 2002/3055* (2013.01); *A61F 2002/30622* (2013.01); *A61F 2002/3092* (2013.01)

(58) Field of Classification Search
CPC .......... A61F 2/30771; A61F 2002/3055; A61F 2002/3092; A61B 17/0642
See application file for complete search history.

(56) References Cited

U.S. PATENT DOCUMENTS

| | | | | |
|---|---|---|---|---|
| 4,289,123 | A | 9/1981 | Dunn | |
| 4,615,338 | A | 10/1986 | Ilizarov | |
| 4,657,550 | A | 4/1987 | Daher | |
| 4,723,540 | A | 2/1988 | Gilmer, Jr. | |
| 5,395,372 | A | 3/1995 | Holt | |
| 5,522,899 | A | 6/1996 | Michelson | |
| 5,620,443 | A | 4/1997 | Gertzbein | |
| 5,683,394 | A | 11/1997 | Rinner | |
| 5,713,899 | A | 2/1998 | Marnay | |
| 5,728,127 | A | 3/1998 | Asher | |
| 5,776,199 | A | 7/1998 | Michelson | |
| 5,947,969 | A | 9/1999 | Errico | |
| 5,951,553 | A | 9/1999 | Betz | |
| 5,980,522 | A | 11/1999 | Koros | |
| 6,156,037 | A | 12/2000 | LeHuec | |
| 6,287,308 | B1 | 9/2001 | Betz | |
| 6,447,547 | B1 | 9/2002 | Michelson | |
| 6,478,823 | B1 | 11/2002 | Michelson | |
| 6,527,803 | B1 | 3/2003 | Crozet | |
| 6,623,484 | B2 | 9/2003 | Betz | |
| 6,821,298 | B1 | 11/2004 | Jackson | |
| 6,984,234 | B2 | 1/2006 | Bray | |
| 7,094,238 | B2 | 8/2006 | Morrison | |
| 7,172,627 | B2 | 2/2007 | Fiere | |
| 7,250,060 | B2 | 7/2007 | Trieu | |
| 7,621,938 | B2 | 11/2009 | Molz, IV | |
| 7,662,186 | B2 | 2/2010 | Bagga | |
| 7,704,279 | B2 | 4/2010 | Moskowitz | |
| 7,727,233 | B2 | 6/2010 | Blackwell | |
| 7,799,060 | B2 | 9/2010 | Lange | |
| 7,833,245 | B2 | 11/2010 | Kaes | |
| 7,955,392 | B2 | 6/2011 | Dewey | |
| 8,062,375 | B2 | 11/2011 | Glerum | |
| 8,070,812 | B2 * | 12/2011 | Keller | A61F 2/44 623/17.11 |
| 8,075,593 | B2 | 12/2011 | Hess | |
| 8,097,037 | B2 | 1/2012 | Serhan | |
| 8,157,842 | B2 * | 4/2012 | Phan | A61B 17/7065 606/249 |
| 8,221,462 | B2 | 7/2012 | Dwyer | |
| 8,226,653 | B2 | 7/2012 | Blackwell | |
| 8,241,330 | B2 | 8/2012 | Lamborne | |
| 8,267,997 | B2 | 9/2012 | Colleran | |
| 8,273,129 | B2 | 9/2012 | Baynham | |
| 8,292,963 | B2 | 10/2012 | Miller | |
| 8,353,913 | B2 | 1/2013 | Moskowitz | |
| 8,377,097 | B2 | 2/2013 | Gordon | |
| 8,388,688 | B2 * | 3/2013 | Moore | A61F 2/4611 606/279 |
| 8,403,959 | B2 | 3/2013 | Dollinger | |
| 8,409,287 | B2 | 4/2013 | Braddock, Jr. | |
| 8,444,697 | B1 * | 5/2013 | Butler | A61F 2/447 623/17.16 |
| 8,454,623 | B2 | 6/2013 | Patel | |
| 8,496,689 | B2 | 7/2013 | Massoudi | |
| 8,545,567 | B1 | 10/2013 | Krueger | |
| 8,603,142 | B2 | 12/2013 | Robinson | |
| 8,603,143 | B2 | 12/2013 | Robinson | |
| 8,690,921 | B2 | 4/2014 | Dwyer | |
| 8,721,686 | B2 | 5/2014 | Gordon | |
| 8,795,367 | B2 | 8/2014 | Zipnick | |
| 8,845,731 | B2 | 9/2014 | Weiman | |
| 8,845,732 | B2 | 9/2014 | Weiman | |
| 8,852,278 | B2 | 10/2014 | Bellas | |
| 8,870,961 | B2 | 10/2014 | Thalgott | |
| 8,882,805 | B1 | 11/2014 | Maccree | |
| 8,894,708 | B2 | 11/2014 | Thalgott | |
| 8,945,184 | B2 | 2/2015 | Hess | |
| 8,961,564 | B2 | 2/2015 | Gordon | |
| 8,979,927 | B2 | 3/2015 | Huntsman | |
| 9,011,493 | B2 | 4/2015 | Zappacosta | |
| 9,039,770 | B2 * | 5/2015 | Aferzon | A61F 2/446 623/17.16 |
| 9,050,143 | B2 | 6/2015 | May | |
| 9,055,981 | B2 | 6/2015 | Lamborne | |
| 9,084,640 | B2 | 7/2015 | Dwyer | |
| 9,107,760 | B2 | 8/2015 | Walters | |
| 9,179,944 | B2 | 11/2015 | Boyer, II | |
| 9,198,774 | B2 | 12/2015 | Pisharodi | |
| 9,204,899 | B2 | 12/2015 | Buttermann | |
| 9,283,084 | B1 * | 3/2016 | O'Hara | A61F 2/4455 |
| 9,283,091 | B2 | 3/2016 | Melkent | |
| 9,308,029 | B2 | 4/2016 | Levieux | |
| 9,375,238 | B2 | 6/2016 | Binder | |
| 9,387,016 | B2 | 7/2016 | Okamoto | |
| 9,393,053 | B2 | 7/2016 | Fessler | |
| 9,402,656 | B2 | 8/2016 | Ingalhalikar | |
| 9,402,739 | B2 | 8/2016 | Weiman | |
| 9,463,091 | B2 | 10/2016 | Brett | |
| 9,566,166 | B2 | 2/2017 | Parry | |
| 9,585,699 | B2 | 3/2017 | Robinson | |
| 9,592,082 | B2 | 3/2017 | Ingalhalikar | |
| 9,622,793 | B1 | 4/2017 | Ponmudi | |
| 9,675,388 | B2 | 6/2017 | Boyer, II | |
| 9,713,537 | B2 | 7/2017 | Bray, Jr. | |
| 9,724,206 | B2 | 8/2017 | Aeschlimann | |
| 9,750,618 | B1 | 9/2017 | Daffinson | |
| 9,763,805 | B2 | 9/2017 | Cheng | |
| 9,795,485 | B2 | 10/2017 | Allain | |
| 9,833,262 | B2 | 12/2017 | Lim | |
| 9,861,399 | B2 | 1/2018 | Rogers | |
| 9,889,020 | B2 | 2/2018 | Baynham | |
| 9,889,022 | B2 | 2/2018 | Moskowitz | |
| 9,956,007 | B2 | 5/2018 | Choi | |
| 9,956,087 | B2 | 5/2018 | Seifert | |
| 9,974,575 | B2 | 5/2018 | Ponmudi | |
| 9,987,144 | B2 | 6/2018 | Seifert | |
| 10,028,740 | B2 | 7/2018 | Moskowitz | |
| 10,076,422 | B2 | 9/2018 | Zappacosta | |
| 10,085,777 | B2 | 10/2018 | Ingalhalikar | |
| 10,136,926 | B2 | 11/2018 | Ponmudi | |
| 10,137,001 | B2 | 11/2018 | Weiman | |
| 10,143,501 | B2 * | 12/2018 | Northcutt | A61B 17/7068 |
| 10,149,703 | B2 | 12/2018 | Moskowitz | |
| 10,182,918 | B2 | 1/2019 | Kim | |

(56) References Cited

U.S. PATENT DOCUMENTS

| | | | | |
|---|---|---|---|---|
| 10,195,045 | B2 | 2/2019 | Muller | |
| 10,231,756 | B2 | 3/2019 | Buss | |
| 10,251,643 | B2 | 4/2019 | Moskowitz | |
| 10,307,265 | B2 | 6/2019 | Sack | |
| 10,307,268 | B2 | 6/2019 | Moskowitz | |
| 10,335,207 | B2 | 7/2019 | Gustine | |
| 10,405,992 | B2 | 9/2019 | Sack | |
| 10,413,426 | B2 | 9/2019 | Parry | |
| 10,420,591 | B2 | 9/2019 | Snell | |
| 10,420,653 | B2 | 9/2019 | Liu | |
| 10,448,979 | B2 | 10/2019 | Fox | |
| 10,463,504 | B2 | 11/2019 | Vestgaarden | |
| 10,478,319 | B2 | 11/2019 | Moskowitz | |
| 10,492,919 | B2 | 12/2019 | Rashbaum | |
| 10,500,058 | B2 | 12/2019 | McKenny | |
| 10,531,961 | B2 | 1/2020 | Dinville | |
| 10,548,647 | B2 | 2/2020 | Ponmudi | |
| 10,555,821 | B2 | 2/2020 | Vestgaarden | |
| 10,588,753 | B2 | 3/2020 | Whipple | |
| 10,603,084 | B1 | 3/2020 | Sanders | |
| 10,660,673 | B2 | 5/2020 | Maly | |
| 10,687,877 | B2 | 6/2020 | Lavigne | |
| 10,695,103 | B2 | 6/2020 | Capote | |
| 10,702,391 | B2 | 7/2020 | Ameil | |
| 10,779,816 | B2 | 9/2020 | Goldstein | |
| 10,849,763 | B2 | 12/2020 | Lauf | |
| 10,864,081 | B2 | 12/2020 | Tyber | |
| 10,925,752 | B2 | 2/2021 | Weiman | |
| 10,945,769 | B2 | 3/2021 | Choi | |
| 10,973,649 | B2 | 4/2021 | Weiman | |
| 11,065,128 | B2 | 7/2021 | Zappacosta | |
| 11,135,069 | B2 | 10/2021 | Eisen | |
| 11,147,685 | B2 | 10/2021 | Zappacosta | |
| 11,259,936 | B2 | 3/2022 | Betz | |
| 11,291,558 | B2 | 4/2022 | Laine | |
| 11,311,388 | B2 | 4/2022 | Frock | |
| 11,311,389 | B2 | 4/2022 | Frock | |
| 11,350,972 | B2 | 6/2022 | Ponmudi | |
| 11,382,670 | B2 | 7/2022 | Gustine | |
| 11,484,415 | B2 | 11/2022 | Kim | |
| 11,534,310 | B2 | 12/2022 | Frock | |
| 11,633,291 | B2 | 4/2023 | Vestgaarden | |
| 11,672,573 | B2 | 6/2023 | Shoshtaev | |
| 11,707,302 | B2 | 7/2023 | Choi | |
| 11,712,343 | B2 | 8/2023 | Predick | |
| 11,723,778 | B1 | 8/2023 | Betz | |
| 11,752,009 | B2 * | 9/2023 | Melchor | A61F 2/447 623/17.11 |
| 11,806,247 | B2 | 11/2023 | Betz | |
| 11,813,175 | B2 | 11/2023 | Zappacosta | |
| 11,883,300 | B2 | 1/2024 | Betz | |
| 12,059,179 | B2 | 8/2024 | Ponmudi | |
| 12,133,664 | B2 | 11/2024 | Frock | |
| 12,144,742 | B2 * | 11/2024 | Betz | A61F 2/4611 |
| 12,263,095 | B2 | 4/2025 | Frock | |
| 2003/0065396 | A1 | 4/2003 | Michelson | |
| 2003/0149482 | A1 | 8/2003 | Michelson | |
| 2003/0235279 | A1 | 12/2003 | Richomme | |
| 2004/0254644 | A1 * | 12/2004 | Taylor | A61F 2/4425 623/17.13 |
| 2005/0159813 | A1 | 7/2005 | Molz | |
| 2005/0165485 | A1 | 7/2005 | Trieu | |
| 2006/0095136 | A1 | 5/2006 | McLuen | |
| 2006/0241764 | A1 | 10/2006 | Michelson | |
| 2007/0010889 | A1 | 1/2007 | Francis | |
| 2008/0114456 | A1 | 5/2008 | Dewey | |
| 2008/0195158 | A1 | 8/2008 | de Villiers | |
| 2008/0294262 | A1 | 11/2008 | Levieux | |
| 2009/0187247 | A1 | 7/2009 | Metcalf, Jr. | |
| 2009/0234389 | A1 | 9/2009 | Chuang | |
| 2010/0030334 | A1 | 2/2010 | Molz, IV | |
| 2010/0070037 | A1 | 3/2010 | Parry | |
| 2010/0131010 | A1 | 5/2010 | Graf | |
| 2010/0312277 | A1 | 12/2010 | Phan | |
| 2010/0318127 | A1 | 12/2010 | Phan | |
| 2011/0118840 | A1 | 5/2011 | Huntsman | |
| 2011/0118842 | A1 | 5/2011 | Bernard | |
| 2011/0125269 | A1 | 5/2011 | Moskowitz | |
| 2011/0144755 | A1 | 6/2011 | Baynham | |
| 2011/0184468 | A1 | 7/2011 | Metcalf, Jr. | |
| 2012/0150229 | A1 | 6/2012 | Hess | |
| 2013/0018472 | A1 * | 1/2013 | Yue | A61F 2/447 623/17.16 |
| 2013/0073045 | A1 | 3/2013 | Vestgaarden | |
| 2013/0103086 | A1 | 4/2013 | Marik | |
| 2013/0184752 | A1 | 7/2013 | Binder | |
| 2013/0245767 | A1 | 9/2013 | Lee | |
| 2013/0274810 | A1 | 10/2013 | Fraser | |
| 2014/0100662 | A1 | 4/2014 | Patterson | |
| 2014/0142628 | A1 | 5/2014 | Traynelis | |
| 2014/0277154 | A1 | 9/2014 | Perry | |
| 2015/0025635 | A1 | 1/2015 | Laubert | |
| 2015/0088256 | A1 | 3/2015 | Ballard | |
| 2015/0105834 | A1 | 4/2015 | Bilger | |
| 2015/0112388 | A1 | 4/2015 | Gordon | |
| 2016/0058480 | A1 | 3/2016 | Laubert | |
| 2016/0106549 | A1 * | 4/2016 | Vestgaarden | A61F 2/447 623/17.16 |
| 2016/0331544 | A1 * | 11/2016 | Braddock, Jr. | A61F 2/447 |
| 2016/0367379 | A1 | 12/2016 | Refai | |
| 2017/0224389 | A1 | 8/2017 | Tatsumi | |
| 2017/0224390 | A1 | 8/2017 | Okamoto | |
| 2017/0311991 | A1 | 11/2017 | Kim | |
| 2018/0028327 | A1 | 2/2018 | Ballard | |
| 2018/0153708 | A1 * | 6/2018 | Melkent | A61F 2/4611 |
| 2018/0243105 | A1 | 8/2018 | Vestgaarden | |
| 2018/0333272 | A1 * | 11/2018 | Mirda | A61F 2/447 |
| 2019/0298421 | A1 | 10/2019 | Capote | |
| 2020/0323642 | A1 | 10/2020 | Vestgaarden | |
| 2021/0000609 | A1 | 1/2021 | Vestgaarden | |
| 2021/0386556 | A1 | 12/2021 | Betz | |
| 2022/0015751 | A1 | 1/2022 | Chevalier | |
| 2022/0168113 | A1 | 6/2022 | Ahmadi | |
| 2022/0387182 | A1 | 12/2022 | Bernard | |
| 2023/0346570 | A1 | 11/2023 | Betz | |
| 2024/0091025 | A1 | 3/2024 | Vestgaarden | |
| 2024/0164909 | A1 | 5/2024 | Betz | |
| 2024/0325163 | A1 | 10/2024 | Betz | |
| 2024/0382317 | A1 | 11/2024 | Horne | |
| 2024/0415666 | A1 * | 12/2024 | Betz | A61F 2/447 |
| 2025/0009395 | A1 | 1/2025 | Frock | |
| 2025/0032158 | A1 | 1/2025 | Gustine | |
| 2025/0107829 | A1 | 4/2025 | McQuinn | |
| 2025/0177159 | A1 | 6/2025 | Goldstein | |
| 2025/0195236 | A1 | 6/2025 | Frock | |
| 2025/0359901 | A1 * | 11/2025 | Schmidt | A61B 17/808 |

FOREIGN PATENT DOCUMENTS

| | | | | |
|---|---|---|---|---|
| AU | 2007317886 | A1 | 5/2008 | |
| CA | 1333209 | C | 11/1994 | |
| DE | 68921482 | | 4/1995 | |
| EP | 0425542 | A1 | 5/1991 | |
| EP | 0637439 | A1 | 2/1995 | |
| EP | 0734702 | A1 | 10/1996 | |
| EP | 2725994 | A1 | 5/2014 | |
| JP | 1991505416 | A | 11/1991 | |
| JP | 2796544 | B2 | 9/1998 | |
| WO | 1990000037 | A1 | 1/1990 | |
| WO | 2004089256 | A1 | 10/2004 | |
| WO | 2005007040 | A1 | 1/2005 | |
| WO | 2005007041 | A1 | 1/2005 | |
| WO | 2006086895 | A1 | 8/2006 | |
| WO | WO-2009091615 | A2 | 7/2009 | |
| WO | WO-2010104496 | A1 * | 9/2010 | A61B 17/7065 |
| WO | 2011057181 | A1 | 5/2011 | |
| WO | 2011057185 | A1 | 5/2011 | |
| WO | 2013043854 | A1 | 3/2013 | |
| WO | 2014145478 | A1 | 9/2014 | |
| WO | 2020209722 | A1 | 10/2020 | |
| WO | 2021230871 | A1 | 11/2021 | |
| WO | 2021257484 | A1 | 12/2021 | |

(56) References Cited

FOREIGN PATENT DOCUMENTS

WO 2022133055 A1 6/2022
WO 2024129794 A1 6/2024

OTHER PUBLICATIONS

Ahn, J., Tabaraee, E., Bohl, D.D., Singh, K., Surgical management of adult spinal deformity: Indications, surgical outcomes, and health-related quality of life. Seminars in Spine Surgery, 29(2), 72-76, 2017, 5 pgs., https://doi.org/10.1053/j.semss.2016.12.001, Chicago, IL, USA.
Magerl, F., Aebi, M., Gertzbein, S.D., Harms, J. Nazarian, S., A comprehensive classification of thoracic and lumbar injuries. European Spine Journal, 3(4), 184-201, 1994, 18 pgs., https://doi.org/10.1007/BF02221591.
Yang, Andres, Non-FInal Office Action for U.S. Appl. No. 15/402,112, mailed Aug. 29, 2018, 9 pgs., USPTO, Alexandria VA, USA.
James Guille, The Feasibility, Safety, and Utility of Vertebral Wedge Osteotomies for the Fusionless Treatment of Paralytic Scoliosis SPINE vol. 28 No. 20s pp. S266-S274, 9 pgs., 2003, Lippincott Williams WIkins, Inc, USA.
Kevin Mccarthy, Clinical Efficacy of the Vertebral Wedge Osteotomy for the Fusionless Treatment of Paralytic Scoliosis SPINE vol. 35 No. 4 pp. 403-410, 8 pgs., 2010 Lippincott, Williams Wilkins, Inc., USA.
Betz RR; Cunningham B; Selgrath C; Drwery T; Sherman MC: Preclinical testing of a wedge-rod system for fusionless correction of scoliosis. Spine (Phila Pa 1976) 28(20S):S275-S278, 2003, 4 pgs., Philadelphia PA, USA.
Betz RR; Mulcahey MJ: New surgical treatments for scoliosis: vertebral body stapling and wedge osteotomies. Viewpoint, Shriners Hospitals for Children, www.shrinershq.org, Sep. 2001, as downloaded from www.SpineUniverse.com on Oct. 15, 2018, 4 pgs., USA.
Didelot, William P.; Kling, Thomas F. Jr.; Lindseth, Richard E.: Anterior Vertebral Osteotomies to Correct Lumbar Scoliosis Without Fusion, Ch. 47. In: Modern Anterior Scoliosis Surgery (Lenke, L.; Betz, R.; Harms, J., eds.), Thieme Medical Publishers, 2004, pp. 693-706, 7 pgs. (2 pgs per sheet), New York, USA.
Rodriquez, Kari, Written Opinion of the International Searching Authority for co-pending PCT Application No. PCT/US21/37285, Aug. 24, 2021, 7 pgs., United States Patent and Trademark Office, Alexandria, VA , USA.
Rodriquez, Kari, International Search Report for PCT Application No. PCT/US21/37285, Aug. 24, 2021, 2 pgs., United States Patent and Trademark Office, Alexandria, VA , USA.
Kamikawa, Tracy L., Office Action for U.S. Appl. No. 17/347,492, Mailed Aug. 6, 2021, 9 pgs., United States Patent and Trademark Office, Alexandria, VA , USA.
Kamikawa, Tracy L., Notice of Allowance for U.S. Appl. No. 17/347,492, Mailed Oct. 18, 2021, 26 pgs., United States Patent and Trademark Office, Alexandria, VA , USA.
Berven, Sigurd H.; Hu, Serena S.; Deviren, Vedat; Smith, Jason; Bradford, David S.: Lumbar End Plate Osteotomy in Adult Patients With Scoliosis, Jun. 2003, Clinical Orthopaedics and Related Research, No. 411, pp. 70-76, 7 pgs., San Francisco, CA, USA.
Kamikawa, Tracy L., Restriction Requirement for U.S. Appl. No. 17/676,609, Mailed May 13, 2022, 8 pgs., United States Patent and Trademark Office, Alexandria, VA , USA.
Kamikawa, Tracy L., Notice of Allowance for U.S. Appl. No. 17/676,609, Mailed Jun. 23, 2022, 24 pgs., United States Patent and Trademark Office, Alexandria, VA , USA.
Negrelli Rodriguez, Christina, Non-FInal Office Action for U.S. Appl. No. 15/404,129, mailed Nov. 5, 2018, 26 pgs., USPTO, Alexandria VA, USA.
Negrelli-Rodriguez, Christina, FInal Office Action for U.S. Appl. No. 15/404,129, mailed Feb. 15, 2019, 20 pgs., USPTO, Alexandria VA, USA.
Negrelli-Rodriguez, Christina, Non-FInal Office Action for U.S. Appl. No. 15/404,129, mailed Aug. 16, 2019, 8 pgs., USPTO, Alexandria VA, USA.
Negrelli-Rodriguez, Christina, Notice of Allowance for U.S. Appl. No. 15/404,129, mailed Nov. 13, 2019, 5 pgs., USPTO, Alexandria VA, USA.
N.H. Hart, S. Nimphius, T. Rantalainen, A. Ireland, A. Siafaikass, R.U. Newton, Mechanical basis of bone strength: influence of bone material, bone structure and muscle action, Journal of Muscoloskeletal and Neuro Interactions, 26 pages, 17(3): 114-139, Sep. 2017, GR.
Kamikawa, Tracy L., Notice of Allowance for U.S. Appl. No. 17/676,609, Mailed Nov. 15, 2022, 5 pgs., United States Patent and Trademark Office, Alexandria, VA , USA.
Waggle, Larry E. Jr., Non-FInal Office Action for U.S. Appl. No. 17/934,874, mailed Dec. 8, 2022, 48 pgs., USPTO, Alexandria VA, USA.
Kamikawa, Tracy L., Notice of Allowance for U.S. Appl. No. 18/051,732, Mailed Feb. 2, 2023, 21 pgs., United States Patent and Trademark Office, Alexandria, VA , USA.
Waggle, Larry E. Jr., Notice of Allowance for U.S. Appl. No. 17/934,874, mailed Feb. 22, 2023, 36 pgs., USPTO, Alexandria VA, USA.
Kamikawa, Tracy L., Non-Final Office Action for U.S. Appl. No. 18/328,876, Mailed Aug. 14, 2023, 22 pgs., United States Patent and Trademark Office, Alexandria, VA , USA.
Matos, Taina, Invitation to Pay Additional Fees for PCT App. No. PCT/US2023/067912, 2 pgs., United States Patent and Trademark Office, Alexandria, Va, USA.
Kamikawa, Tracy L., Final Office Action for U.S. Appl. No. 18/328,876, Mailed Oct. 24, 2023, 28 pgs., United States Patent and Trademark Office, Alexandria, VA , USA.
Kamikawa, Tracy L., Notice of Allowance for U.S. Appl. No. 18/328,876, Mailed Jan. 2, 2024, 26 pgs., United States Patent and Trademark Office, Alexandria, VA , USA.
Matos, Taina, International Search Report and Written Opinion for PCT App. No. PCT/US2023/067912, Mailed Jan. 22, 2024, 16 pgs., United States Patent and Trademark Office, Alexandria, VA, USA.
Salima Filali, European Patent Office, Supplementary European Search Report and European search opinion, App. No. 21824991.0, Jun. 17, 2024, 11 pgs., European Patent Office, Munich, Germany.
Kamikawa, Tracy L., Non-Final Office Action for U.S. Appl. No. 18/424,843, Mailed Dec. 17, 2024, 19 pgs., United States Patent and Trademark Office, Alexandria, VA , USA.
Kamikawa, Tracy L., Non-Final Office Action for U.S. Appl. No. 18/736,212, Mailed Feb. 7, 2025, 29 pgs., United States Patent and Trademark Office, Alexandria, VA , USA.
Kamikawa, Tracy L., Final Office Action for U.S. Appl. No. 18/424,843, Mailed Apr. 24, 2025, 24 pgs., United States Patent and Trademark Office, Alexandria, VA , USA.
Waggle Jr., Larry E, Non-Final Office Action for U.S. Appl. No. 18/337,388, Mailed May 23, 2025, 12 pgs., United States Patent and Trademark Office, Alexandria, VA , USA.
Cesari, Aude, Intention to grant for European Patent Office Patent Application No. 21824991.0, Mailed Apr. 4, 2025, 8 pgs., European Patent Office, Berlin, Germany.
Hablas, Mouhammad, Examination Report for Intellectual Property Australia Patent Application No. 2021292075, Examination Report No. 1, Mailed May 22, 2025, 3 pgs., Intellectual Property Australia, Australia.
Kamikawa, Tracy L., Non-Final Office Action for U.S. Appl. No. 18/736,212, Mailed Jul. 2, 2025, 26 pgs., United States Patent and Trademark Office, Alexandria, VA , USA.
Waggle Jr., Larry E, Notice of Allowance for U.S. Appl. No. 18/337,388, Mailed Jul. 29, 2025, 12 pgs., United States Patent and Trademark Office, Alexandria, VA , USA.
Kamikawa, Tracy L., Non-Final Office Action for U.S. Appl. No. 18/424,843, Mailed Dec. 1, 2025, 20 pgs., United States Patent and Trademark Office, Alexandria, VA , USA.
Kamikawa, Tracy L., Final Office Action for U.S. Appl. No. 18/736,212, Mailed Dec. 16, 2025, 23 pgs., United States Patent and Trademark Office, Alexandria, VA , USA.

(56) References Cited

OTHER PUBLICATIONS

Kim, Harry, International Search Report and Written Opinion for PCT App. No. PCT/US2025/045274, Mailed Jan. 6, 2026, 22 pgs., United States Patent and Trademark Office, Alexandria, VA, USA.
Kim, Harry, International Search Report and Written Opinion for PCT App. No. PCT/US2025/045275, Mailed Jan. 6, 2026, 21 pgs., United States Patent and Trademark Office, Alexandria, VA, USA.
Kamikawa, Tracy L., Restriction Requirement for U.S. Appl. No. 19/322,646, Mailed Feb. 25, 2026, 7 pgs., United States Patent and Trademark Office, Alexandria, VA , USA.
Kamikawa, Tracy L., Non-Final Office Action for U.S. Appl. No. 18/813,627, Mailed Mar. 19, 2026, 14 pgs., United States Patent and Trademark Office, Alexandria, VA , USA.
Kamikawa, Tracy L., Final Office Action for U.S. Appl. No. 18/347,655, Mailed Apr. 1, 2026, 15 pgs., United States Patent and Trademark Office, Alexandria, VA , USA.
Kamikawa, Tracy L., Non-Final Office Action for U.S. Appl. No. 19/322,646, Mailed Apr. 28, 2026, 11 pgs., United States Patent and Trademark Office, Alexandria, VA , USA.
Kamikawa, Tracy L., Final Office Action for U.S. Appl. No. 18/424,843, Mailed Apr. 28, 2026, 26 pgs., United States Patent and Trademark Office, Alexandria, VA , USA.
Kamikawa, Tracy L., Non-Final Office Action for U.S. Appl. No. 18/736,212, Mailed Apr. 17, 2026, 27 pgs., United States Patent and Trademark Office, Alexandria, VA , USA.
European Patent Office, Search Report for EP App. No. 23820547. 0/PCT/US2023/067912, Mailed Apr. 29, 2026, 10 pgs., European Patent Office, 80298, Munich, Germany.
Kamikawa, Tracy L., Final Office Action for U.S. Appl. No. 18/813,627, mailed Jul. 6, 2026, 12 pgs., United States Patent and Trademark Office, Alexandria, VA, USA.
Kamikawa, Tracy L., Notice of Allowance for U.S. Appl. No. 18/347,655, mailed Jul. 28, 2026, 14 pgs., United States Patent and Trademark Office, Alexandria, VA, USA.
Kamikawa, Tracy L., Notice of Allowance for U.S. Appl. No. 18/424,843, mailed Jul. 28, 2026, 15 pgs., United States Patent and Trademark Office, Alexandria, VA, USA.
Hammond, Ellen Christina, Notice of Allowance for U.S. Appl. No. 19/322,647, mailed Jul. 1, 2026, 8 pgs., United States Patent and Trademark Office, Alexandria, VA, USA.
Kamikawa, Tracy L., Final Office Action for U.S. Appl. No. 19/322,646, mailed Aug. 12, 2026, 8 pgs., United States Patent and Trademark Office, Alexandria, VA, USA.
Hablas, Mouhammad, Examination Report for New Zealand Intellectual Property Office Patent Application No. 795189, Patent Examination Report No. 1, Mailed Jun. 22, 2026, 3 pgs., New Zealand Intellectual Property Office, New Zealand.

* cited by examiner

IMPLANT SYSTEMS AND METHODS FOR STABILIZING A BONE FROM AN ANTERIOR APPROACH

CROSS-REFERENCE TO RELATED APPLICATIONS

This application claims benefit to U.S. Pat. App. No. 63/692,693, filed on Sep. 9, 2024; this application claims benefit to U.S. Pat. App. No. 63/692,618, filed Sep. 9, 2024; this application is a continuation in part of PCT App. No. PCT/US25/45275, filed Sep. 7, 2025; this application is a continuation in part of PCT App. No. PCT/US25/45274, filed Sep. 7, 2025; PCT App. No. PCT/US25/45275 claims benefit to U.S. Pat. App. No. 63/692,693; PCT App. No. PCT/US25/45275 claims benefit to U.S. Pat. App. No. 63/692,618; PCT App. No. PCT/US25/45274 claims benefit to U.S. Pat. App. No. 63/692,693; PCT App. No. PCT/US25/45274 claims benefit to U.S. Pat. App. No. 63/692,618; the entire contents of which are incorporated herein by reference.

STATEMENT REGARDING FEDERALLY SPONSORED RESEARCH OR DEVELOPMENT

Not applicable.

REFERENCE TO SEQUENCE LISTING, A TABLE, OR A COMPUTER PROGRAM LISTING COMPACT DISC APPENDIX

Not applicable.

BACKGROUND OF THE INVENTION

Aspects of the present disclosure relate to orthopedic implants. Embodiments of the orthopedic implants may be used as spinal implants to stabilize vertebra from an anterior approach to the spine. Embodiments of the implants may be configured to augment the vertebral body or fuse multiple vertebral bodies to decompress neural elements and alter the alignment of the spine.

BRIEF SUMMARY OF THE INVENTION

The systems, methods, and devices of the disclosure each have several aspects, no single one of which is solely responsible for its desirable attributes. Without limiting the scope of this disclosure as expressed by the claims which follow, some features will now be discussed briefly. After considering this discussion, and particularly after reading the section entitled "Detailed Description" one will understand how the features of this disclosure provide advantages that include improved communications between access points and stations in a wireless network.

The following summary is included only to introduce some concepts discussed in the Detailed Description of the Invention below. This summary is not comprehensive and is not intended to delineate the scope of protectable subject matter, which is set forth by the claims presented at the end.

Within this description, the terms far, distal, and contralateral are used interchangeably and are intended to be interpreted as defining that one thing is distant from another such as distance from a point of origin, situated away from a point of origin, and pertaining to the other side. Also, the terms near, proximal and ipsilateral are used interchangeably within this description and are intended to be interpreted as defining a short distance away from another such as away from a point of origin, situated toward a point of origin and belonging to or occurring on the same side of a body.

In some of the disclosed embodiments of an implant system having a cage and securing element, the securing element is translatable or slidable relative to portions of the cage. The translation and slidability of the securing element relative to the cage provides several features to the implant system. This translatable or slidable configuration allows portions of the securing element, such as a staple, to slide in and out, towards and away from portions of the cage. As an example with the securing element being a staple, this allows for better control of the alignment, location and positioning of the staple shaft, and when the staple shaft is operably coupled to the staple head in a way that allows the staple head to rotate with the staple shaft, this allows for better control of the alignment and location and positioning of the staple head. This control allows the staple head to be moved through alignments and locations and positions that better accommodate the surface of the bone to better secure the staple and implant device to the bone. This control also allows the implant system to better accommodate use and implanting from surgical approach trajectories that are less invasive than other approach trajectories to provide better surgical outcomes.

In some of the disclosed embodiments of an implant system, the implant system is secured to a bone with a compressive force. The ability of the implant system to secure the implant device with a compression force from opposite sidewalls of a bone provides a more secure anchoring of the implant device to the bone as compared to anchoring from one side of the bone. The orientation of the implant device when implanted may also provide a platform on the device to anchor additional devices such as tether screws, tulip head screws and rods or tethers or cords to the implant device.

The configuration of the implant system components also provides the ability for the implant device to be implanted from different approach trajectories that take advantage of the surgical benefits of approach trajectories such as anterior or anterior lateral or oblique anterior. Direct anterior approach trajectories are applicable to L5-S1 of the lumbar and sacral spine and applicable to other spine locations such as but not limited to L4-L5, L3-L4, all lumbar segments, lower thoracic and all cervical.

According to an aspect of the invention, there is provided an orthopedic implant device comprising a cage, a first staple and a second staple, and the first staple and the second staple are each movable relative to the cage whereby the first staple and the second staple are each configured to move from an insertion position to a stabilized position.

In some embodiments, the orthopedic implant device is configured to be positioned from one of an anterior approach trajectory, an anterior lateral approach trajectory, or an anterior oblique approach trajectory relative to a bone. In some embodiment, the implant device is configured to be used in an anterior lumbar interbody fusion (ALIF) procedure.

According to one aspect of the invention, there is provided an orthopedic implant device having a cage, a securing element, and the securing element is movable relative to the cage whereby the securing element is configured to move from an insertion position to a stabilized position.

According to one aspect of the invention, an orthopedic implant device is provided comprising: a cage; a securing element; and the securing element is movable relative to the cage whereby the securing element is configured to move from an insertion position to a stabilized position.

Embodiments may include one or more of the following features. In some embodiments, the securing element is configured to be movable about an axis that is non-parallel to an approach trajectory of the orthopedic implant device. In some embodiments, the securing element comprises a first staple and a second staple. In some embodiments the orthopedic implant device may include a coupling mechanism configured to move each of the first staple and the second staple. In some embodiments, the coupling mechanism comprises an inner nut nested in an outer nut; the inner nut configured to move each of the first staple and the second staple from an insertion position to an extended position; the inner nut configured to move to move each of the first staple and the second staple from the extended position to a deployed position; and the outer nut configured to secure the first staple and the second staple to a locked position. In some embodiments the orthopedic implant device may include a coupling mechanism configured to move each of the first staple and the second staple wherein: the first staple has a first staple head positioned near a first lateral side of the cage; the second staple has a second staple head positioned near a second lateral side of the cage; and the coupling mechanism is positioned on a proximal side of the cage where the coupling mechanism may be manipulated by a staple drive handle assembly from the proximal side of the cage. In some embodiments, the orthopedic implant device is configured to be positioned from one of an anterior approach trajectory, an anterior lateral approach trajectory, or an anterior oblique approach trajectory relative to a bone. In some embodiments, the orthopedic implant device may include a coupling mechanism configured to move each of the first staple and the second staple where the coupling mechanism is configured to be movable by a rotation about a coupling mechanism rotation axis that is aligned in a non-parallel orientation to a staple rotation axis of one of the first staple or the second staple. In some embodiments, the coupling mechanism rotation axis is generally transverse to the staple rotation axis of one of the first staple or the second staple. In some embodiments, the orthopedic implant device is configured as an implant device for a vertebra. In some embodiments, the orthopedic implant device is configured to be used in an anterior lumbar interbody fusion (ALIF) procedure. In some embodiments, the vertebra comprises a first vertebra having a vertebral body having a superior endplate where the cage is configured to extend across the superior endplate of the first vertebra; the cage is also configured to extend across an inferior endplate of a vertebral body of a second vertebra; and the first staple and the second staple are configured to secure the orthopedic implant device to a lateral sidewall of the vertebral body of the first vertebra and a lateral sidewall of the vertebral body of the second vertebra. In some embodiments, the first vertebra comprises an S1 vertebra of a sacral spine; and the second vertebra comprises an L5 vertebra of a lumbar spine where the first staple and the second staple are configured to secure the orthopedic implant device to a posterior sidewall of the vertebral body of the L5 vertebra and the posterior sidewall of the vertebral body of the S1 vertebra. In some embodiments, the first staple and the second staple each have a staple head positioned outside of an outer wall of the cage. In some embodiments, the first staple and the second staple are configured to engage an outside surface of a first sidewall and a second sidewall of a vertebral body of the vertebra. In some embodiments, a relative positioning of the first staple and the second staple in the stabilized position is at a shorter distance than the relative position of the first staple and second staple in a deployed position. In some embodiments, the first staple and the second staple each have a staple head positioned within an outer wall of the cage. In some embodiments, the first staple and the second staple are configured to engage a vertebral body of the vertebra inside a first sidewall and a second sidewall of the vertebral body. In some embodiments, a relative positioning of the first staple and the second staple in the stabilized position is at a greater distance than the relative position of the first staple and the second staple in a deployed position. In some embodiments, the orthopedic implant device is configured to be used in an anterior lumbar intrabody fusion (ALIF) procedure. In some embodiments, the vertebra comprises a vertebra having undergone an osteotomy creating a first vertebral body portion and a second vertebral body portion and the first staple and the second staple are configured to secure the orthopedic implant device to the first vertebral body portion and the second vertebral body portion. In some embodiments, the vertebra comprises a first (S1) vertebra of a sacral spine. In some embodiments, the vertebra comprises at least one of a vertebra selected from the group consisting of: an L1 vertebra of a lumbar spine; an L2 vertebra of the lumbar spine; an L3 vertebra of the lumbar spine; an L4 vertebra of the lumbar spine; an L5 vertebra of the lumbar spine; a thoracic vertebra of a thoracic spine; and a cervical vertebra of a cervical spine. In some embodiments, the cage comprises a middle section, a first lateral section and a second lateral section; the first lateral section and the second lateral section are each moveable relative to the middle section; the first lateral section is configured to move with the first staple when the first staple moves from the insertion position to an extended position; and the second lateral section is configured to move with the second staple when the second staple moves from the insertion position to an extended position. In some embodiments, a portion of the cage comprises a lattice surface configuration. In some embodiments, the securing element comprises a first staple and a second staple; the first staple comprises a first staple head and a first staple shaft; the second staple comprises a second staple head and a second staple shaft; and the first staple shaft and the second staple shaft are configured to be rotated to move the first staple head and the second staple head. In some embodiments, the securing element comprises a first staple and a second staple; the first staple comprises a first staple head and a first staple shaft; the second staple comprises a second staple head and a second staple shaft; and the first staple shaft and the second staple shaft are configured to be translated to move the first staple head and the second staple head. In some embodiments, the securing element comprises a first staple and a second staple; and the first staple and the second staple are movable relative to the cage where the first staple and the second staple are configured to move from the insertion position to a deployed position. In some embodiments, the securing element comprises a first staple and a second staple; and a relative positioning of the first staple and the second staple in the stabilized position is at a shorter distance than the relative position of the first staple and the second staple in a deployed position. In some embodiments, the securing element comprises a single staple.

According to one aspect of the invention, there is provided an orthopedic implant device comprising: a cage having a longitudinal axis extending from a proximal side to a distal side; the cage having a transverse axis extending from a first lateral side to a second lateral side; one or more staple each having a staple head; a coupling mechanism configured to move the one or more staple in a non-parallel orientation to the longitudinal axis of the cage; the one or more staple and the cage operably coupled where the one or more staple head is positioned adjacent to one of the first lateral side of the cage or the second lateral side of the cage; where the one or more staple head is configured to be secured to a first bone portion and a second bone portion; and where the cage is secured to the first bone portion and the second bone portion.

Embodiments may include one or more of the following features. In some embodiments of the orthopedic implant device, the one or more staple is configured to move from a deployed position to a stabilized position. In some embodiments, the coupling mechanism is configured to rotate about a coupling mechanism rotation axis that is aligned in a non-parallel orientation to a staple rotation axis of the one or more staple. In some embodiments, the one or more staple head is positioned adjacent to one of the first lateral side of the cage or the second lateral side of the cage; and the coupling mechanism is positioned on a proximal side of the cage where the coupling mechanism may be manipulated by a staple drive handle assembly from the proximal side of the cage. In some embodiments, the coupling mechanism rotation axis is generally transverse to the staple rotation axis of the one or more staple. In some embodiments, the one or more staple comprises a first staple and a second staple. In some embodiments, the one or more staple comprises a first staple on a first lateral side of the cage and a second staple on an opposing second later side of the cage. In some embodiments, the one or more staple is configured to move from a deployed position to a stabilized position; and a relative positioning of the one or more staple from a mid-point of the cage in a stabilized position is at a shorter distance than the relative position of the one or more staple from the midpoint of the cage in the deployed position. In some embodiments, the one or more staple head is positioned outside of an outer wall of the cage. In some embodiments, the one or more staple is configured to move from a deployed position to a stabilized position; and a relative positioning of the one or more staple from a mid-point of the cage in the stabilized position is at a greater distance than the relative position of the one or more staple from the midpoint of the cage in the deployed position. In some embodiments, the one or more staple head is positioned inside of an outer wall of the cage. In some embodiments, the coupling mechanism comprises an inner nut nested in an outer nut; the inner nut configured to move the one or more staple from an insertion position to a deployed position; the inner nut configured to move the one or more staple from the insertion position to a stabilized position; and the outer nut configured to secure the one or more staple in a locked position.

According to one aspect of the invention, there is provided a method to secure an orthopedic implant device to a first bone portion and a second bone portion, the method comprising: providing an orthopedic implant device comprising a cage and one or more staple; the cage movably coupled to the one or more staple; positioning the cage into an opening between the first bone portion and the second bone portion; and moving one of the one or more staple to secure the cage to the first bone portion and the second bone portion.

Embodiments may include one or more of the following features. In some embodiments of the method, the one or more staple is moved by a coupling mechanism; and the step of moving one of the one or more staple to secure the cage to the first bone portion and the second bone portion comprises: engaging the coupling mechanism to move the one or more staple from an insertion position to a deployed position, and engaging the coupling mechanism to move the one or more staple from the deployed position to a stabilized position where the cage is secured to the first bone portion and the second bone portion. In some embodiments of the method, the step of engaging the coupling mechanism to move the one or more staple from an insertion position to a deployed position comprises rotating the coupling mechanism about a coupling mechanism rotation axis where the one or more staple rotates about a staple rotation axis to move the one or more staple from the insertion position to the deployed position; and the coupling mechanism rotation axis is non-parallel to the staple rotation axis. In some embodiments of the method, the step of positioning the cage into an opening between the first bone portion and the second bone portion comprises positioning, from an anterior position to the cage, the cage into an opening between the first bone portion and the second bone portion. In some embodiments of the method, the first bone portion comprises a first bone portion of a vertebral body after an osteotomy and the second bone portion comprises a second bone portion of the vertebral body. In some embodiments of the method, the first bone portion comprises a first vertebral body and the second bone portion comprises a second vertebral body. In some embodiments of the method, the method comprises a method to perform an Anterior Lumbar Interbody Fusion (ALIF). In some embodiments of the method, the step of engaging the coupling mechanism to move the one or more staple from the deployed position to a stabilized position comprises rotating the coupling mechanism about a coupling mechanism rotation axis where the one or more staple translates along a staple rotation axis to move the one or more staple from the deployed position to the stabilized position; and the coupling mechanism rotation axis is non-parallel to the staple rotation axis. In some embodiments of the method, the one or more staple is moved by a coupling mechanism; the coupling mechanism comprises an inner nut and an outer nut; the inner nut configured to move the one or more staple from an insertion position to a stabilized position; the outer nut configured to secure the one or more staple in a locked position; and the step of moving one of the one or more staple to secure the cage to the first bone portion and the second bone portion comprises: engaging the outer nut to move the coupling mechanism from a locked position to a translation position, engaging the inner nut to move the one or more staple from the insertion position to an extended position, engaging the outer nut to move the coupling mechanism from the translation position to a rotation position, engaging the inner nut to move the one or more staple from the extended position to a deployed position, engaging the outer nut to move the coupling mechanism into the translation position, engaging the inner nut to move the one or more staple from the extended position to a stabilized position where the cage is secured to the first bone portion and the second bone portion, and engaging the outer nut to move the coupling mechanism into a locked position where the cage is locked in a locked position to the first bone portion and the second bone portion.

Intravertebral Applications

Intravertebral use of the disclosed implant system is intended to restore foraminal height and treat vertebral body wedging, which result from microfractures and collapse of the vertebral body endplates. These microfractures occur because the collapsed disc creates abnormal stress areas in the vertebral body. The resultant vertebral body wedging, secondary to the microfractures, creates both sagittal and coronal deformity, causing back pain through misaligned facet joints and leg pain due to foraminal stenosis. The source of the back pain can be confirmed by injecting diagnostic local anesthetic agents around the painful facet joint and/or nerve roots. Correction of these deformities in the vertebral body via osteotomy and placement of the vertebral implant can reduce the back and leg pain by realigning the facet joints and opening the foramen in this select group of patients. This is analogous to the use of high tibial osteotomies for treatment of knee arthritis. The implant system and implant device design allows for careful and patient-specific sagittal and coronal alignment correction to prevent the clinical outcomes of misalignment.

This osteotomy procedure and implant device can relieve pain symptoms while maintaining lumbar spine mobility and prevent or delay adjacent level disease. The implant device does not have any motion itself but reestablishes proper spinal alignment while preserving the intervertebral disc above and below the operated level.

With the disclosed implant system, a vertebral body osteotomy stabilized with the implant device can correct the wedged segment of the spine through the vertebral body. This opens the foramen and relieves the pinched nerve and therefore relieves the patient's radiculopathy symptoms. The implant system and implant device design allows for careful and patient-specific sagittal and coronal correction to prevent the clinical outcomes of spinal misalignment.

The disclosed implant system can bridge the gap between a minimally invasive decompression without fusion and more extensive decompressions requiring a fusion procedure and lead to an improved quality of life when compared to current standard surgical techniques and technology. The patient will have relief from back and/or leg pain without a loss of spine mobility, which can significantly reduce or eliminate the risk of adjacent level accelerated degeneration in the other levels of the spine. The custom alignment created with the implant device can prevent the clinical outcomes of spinal misalignment.

Examples of the implant system may comprise a vertebral implant device configured to alter a distance between a superior endplate surface plane and an inferior endplate surface plane of a vertebral body.

Intervertebral Applications

Intervertebral use of the disclosed implant system is intended to fuse opposing vertebral bodies to eliminate painful motion and/or to restore anatomic alignment, height and stability to the spine following a spinal decompression. This fusion eliminates motion between vertebrae and also prevents the irritation and stretching of nerves and surrounding ligaments and muscles.

Intervertebral use of the implant system generally provides an implant that is able to be secured to the inferior and superior endplates of two opposing vertebrae to facilitate a fusion. Dimensions of components of the implant system may also be shaped to provide patient-specific sagittal and coronal alignment to prevent the clinical outcomes of misalignment.

In some examples, the implant system comprises an intervertebral implant device configured to join one vertebral body to another vertebral body.

Applications with Other Joints

Implant systems similar in design to the above implant systems may be used as an arthrodesis implant system in an arthrodesis procedure for other joints. As done for the joining of two vertebrae, an implant system and implant device may be provided that is configured to be secured to opposing sides of adjoining bones in a joint to fuse those bones. The stabilization may also be used to correct alignment of the bones of the joint.

In some examples of the implant system, the implant system comprises an arthrodesis implant device configured to join one bone to another bone.

Other objects, features, and advantages of the systems and techniques disclosed in this specification will become more apparent from the following detailed description of embodiments in conjunction with the accompanying drawings.

BRIEF DESCRIPTION OF THE SEVERAL VIEWS OF THE DRAWINGS

In order that the manner in which the above-recited and other advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

Figure 1A:
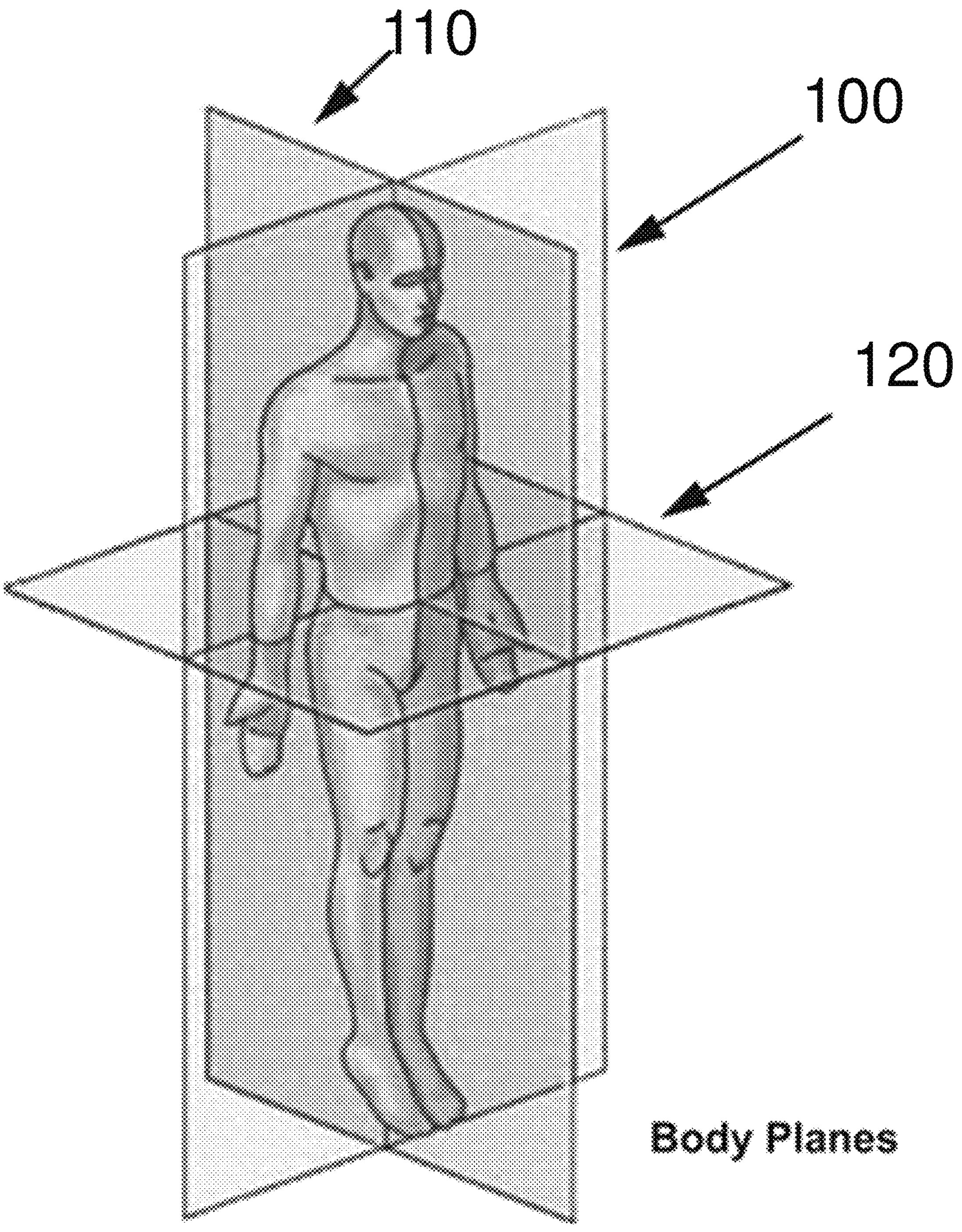
FIG. 1A shows the sagittal, coronal, and transverse planes of the human body.

COPYRIGHT NOTICE: A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. The following notice applies: Copyright @ 2020-2025, Foundation Surgical Group, Inc., All Rights Reserved.

Implant systems and methods of use will now be described in detail with reference to the accompanying drawings. Notwithstanding the specific examples set forth below, all such variations and modifications that would be envisioned by one of ordinary skill in the art are intended to fall within the scope of this disclosure. The implant systems and methods may be used as orthopedic implant systems such as, but not limited to, an intravertebral implant system for use in intravertebral applications, an intervertebral implant system for use in intervertebral applications and an implant system for arthrodesis procedures for other joints throughout a mammalian body. The implant systems and methods may comprise an orthopedic implant device such as, but not limited to, an intravertebral implant device, an intervertebral implant device or an implant device for arthrodesis procedures for other joints throughout the body.

Foraminal narrowing is a specific type of spinal stenosis, a spinal condition that occurs when the open spaces between the vertebra (the foramina) narrow. The foramina are bony passageways located between the vertebrae on either side of the spine. Their primary purpose is to provide an exit path for nerves leaving the spinal cord and traveling to other parts of the body.

Minimally invasive spine (MIS) surgery without fusion is generally intended to relieve pressure being applied to the spinal nerves-often a result of conditions such as spinal instability, bone spurs, herniated discs, scoliosis, or spinal tumors. In cases where extensive decompressions are required to accomplish the goal of relieving pain, a fusion may become necessary.

Fusion of opposing bones of a joint results in a permanent connection of the bones of the joint to eliminate motion between them. All fusions, including spinal fusion, involves techniques designed to mimic the normal healing process of broken bones where an implant device may be used to hold the vertebrae together, so they can heal into one solid and immobile unit.

In general, when assembled and implanted in the vertebral body, the external surface dimension and configuration of the implant system and implant device, when used as a vertebral implant device, are able to correct the relative orientation of a superior endplate surface plane relative to an inferior endplate surface plane of one or more vertebral body to alter the alignment of the spine. Embodiments of the disclosed implant systems may be configured to correct vertebral body deformity in the coronal, sagittal, and axial plane (if needed) and any combination thereof.

The system may be suitable for indirect foraminal decompressions that require more than a MIS procedure but less than a large decompression and fusion. Embodiments of the disclosed implant systems may be used for 1 and 2 vertebral body interventions and may be used with multiple vertebrae to address multiple vertebrae in the spine.

In some embodiments, the implant device generally acts as an opening wedge osteotomy spacer and uses the shape of implant components, such as cage surface planes, to alter the alignment of the vertebral body of a mammalian body.

Referring to FIG. 1A showing the sagittal 110, coronal 100 and transverse 120 planes of the human body, embodiments may be used to correct alignment of the spine in the sagittal (110) and coronal (100) planes.

Figure 1B:
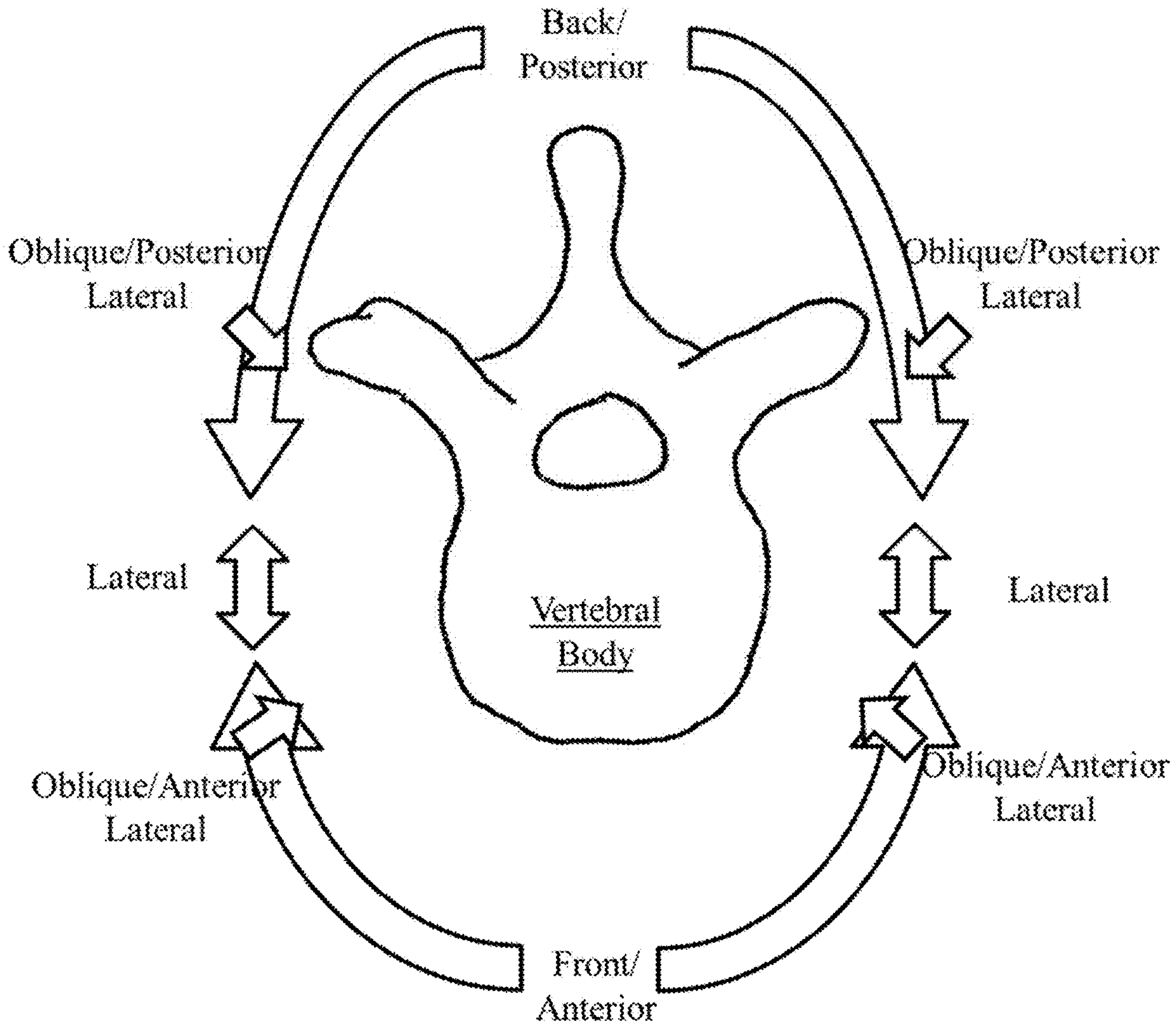
FIG. 1B illustrates the different axis and placement approaches used with an example of an implant systems.

Referring to FIG. 1B, the implant system may be inserted and positioned at and from different angles relative to the vertebral body. The placement and configuration of the implant components dictate the different alignment surface angles of the vertebral bodies. For example, some embodiments of the implant system may be implanted through anterior (front), oblique or lateral (left/right) approaches.

In some embodiments, the implant system is configured to preserve the spinal vascular system.

In some embodiments, the configuration of the implant system allows for stabilization and bone fusion within the vertebral body after placement.

In some embodiments, the implant system is configurable. For example, the implant system may be configured to provide different alignments to vertebral bodies and the spine. For example, the implant system may provide configurable dimensions such as different height and angles of the cage surfaces to provide different cage surface planes and different sagittal and coronal angular correction when positioned in the vertebral body.

In some embodiments, the implant system may be a modular system including a self-stabilizing cage which includes deployable and fixed securing elements, anchoring elements such as bone fixation screws attachable to the anchor frame and any one of many anti-backout features known in the art to prevent the bone fixation screws from projecting out of the anchor frame.

In some embodiments, the implant system may be prepacked with bone graft (autogenous, allogenic, or synthetic) and the implant system may be configured to allow additional graft material to be post-packed, injected or otherwise placed after positioning of the implant within the vertebral body.

In some embodiments, provisions may be made to couple the implant system to other constructs such as rod/cord-screw systems, flexible tethers, and plate systems.

In some embodiments, the implant system generally comprises a cage with a securing element. In some embodiments, the securing element comprises one or more staple. With embodiments having more than one staple, the staples may be on opposing sides of the cage to secure the cage to bone. In some embodiments the one or more staple may have features that allow the staples to be inserted, extended, deployed, and stabilized or secured to the bone. In some embodiments the one or more staple is generally positioned outside of the cage and the implant system is secured to the bone by retracting the staple towards the cage whereby the staple engages the sidewalls of the bone. In some embodiments, the one or more staple is generally positioned within the implant cage and is configured for intraosseous deployment to secure the implant system to the bone.

In some embodiments, the cage generally provides the structural support for the implant device to define and maintain the desired spacing between bones or bone portions after the implanting the implant device. In some embodiments, the case is a unity cage. In some embodiments, the cage is an extendable cage having a middle section, a first lateral section and a second lateral section. The first lateral section and the second lateral section are each moveable relative to the middle section whereby the first lateral section is configured to move the first staple from the insertion position to an extended position and the second lateral section is configured to move the second staple from the insertion to an extended position. In some embodiments, the first staple comprises a first staple head and a first staple shaft, the second staple comprises a second staple head and a second staple shaft, and each of the first staple shaft and the second staple shaft are configured to be rotated relative to the cage to move each of the first staple head and the second staple head from the extended position to a deployed position. In some embodiments, the first lateral section and the second lateral section are further configured to move the first staple head and the second staple head from the deployed position to the stabilized position.

In some embodiments, the one or more staple of the implant system may have extension, deployment and retracting features that allow the staple to be moved through multiple positions to secure the implant device to the bone. The movement features may allow the one or more staple to be easily moved between an insertion position, an extended position, a deployed position, and a stabilized position. For the one or more staple, these different positions of the staple describe both the rotational alignment of the staple head and the location of the staple head relative to other elements of the implant device. The staple head may be any shape and the staple head may have a length representing the dimension of the staple head with the longest distance from the longitudinal axis of the staple or the dimension from the longitudinal axis of the staple to the staple tines. In the example embodiments shown, the staple head generally has a length extending from the longitudinal axis of the staple to the ends of the staple head with the staple tines.

In some embodiments, the one or more staple moves in a coordinated fashion in other embodiments, they can be moved independently.

Insertion position: In the insertion position, alignment of the length of the staple head is in a neutral alignment, generally the orientation of the length of the staple head being coplanar or parallel to the top or bottom surface plane of the cage and extending along the lateral sides of the cage. In this position, the lateral location of the staple head relative to a lateral axis of the cage (lateral side to lateral side) is the location as the implant device is being positioned for implanting. In some embodiments, the lateral location of the staple head is generally positioned in a non-extended/insertion location close to, or near, a lateral side of the cage. For embodiments with the staple outside of the cage, the insertion position generally positions the staple adjacent to, or near, and outside of the outer lateral wall of the cage. For embodiments with the staple inside of the cage, the insertion position generally positions the staple within the outer lateral wall of the cage. In some embodiments, the insertion location of the staple head position may have the staple head in an extended location extended away from the cage. In some embodiments, portions of the staple head may be received in a protective recess on the cage. These insertion positions may protect or cover the staple tines during insertion into the patient.

Extended position: In the extended position, the alignment of the staple head is in the neutral alignment, generally parallel to the surface planes of the cage. In this position, the lateral location of the staple head relative to the cage lateral axis is in an extended location extended away from a center of the cage and away from an opposing staple. For embodiments with staple outside of the cage, the extended position generally extends the location of the staple head from the cage laterally so that the staple head and the staple tines extend away from the center of the cage and beyond the sidewalls of the bone. For embodiments with an extendable staple inside of the cage, the extended position generally extends the location of the staple head away from the center of the cage.

Deployed position: In the deployed position, the staple head is rotated to a non-neutral alignment that is other than parallel to the top or bottom surface plane of the cage. In this position, the non-neutral alignment of the staple head may be at any angle relative to the insertion and extended position sufficient to allow the staple tines of the staple to be positioned to engage the sidewalls of the bone above and below the cage. In the deployed position, the lateral location of the staple head relative to the lateral axis of the cage is in: (1) for embodiments with an extendable staple outside of the cage, an extended location extended away from the center of the cage sufficient to allow the staple tines of the staple head to extend beyond the sidewalls of the bone, or (2) for embodiments with an extendable staple within the cage, at an extended location extended away from the insertion position but within the sidewalls of the bone, or (3) for embodiments with a non-extendable staple within the cage, generally at the lateral location of the insertion position, or (4) for embodiments with a non-extendable staple outside of the cage, generally at the lateral location of the insertion position. Preferably, the non-neutral alignment in the deployed position is about 90 degrees from the neutral alignment to maximize engagement with the bone.

Stabilized position: In the stabilized position, alignment of the length of the staple head is not parallel to the surface planes of the cage and sufficient to allow the staple tines of the staple head or a portion of the staple head to engage the bone. In this position, the alignment of the staple head is generally in the non-neutral alignment of the deployed position. In the stabilized position, the lateral location of the staple head relative to the cage is in: (1) for embodiments with an extendable staple outside of the cage, a retracted location retracted towards the cage sufficient to allow the staple tines of the staple head to engage or embed themselves in the bone to mechanically engage and stabilize the staple head and the cage to the bone, or (2) for embodiments with the extendable staple within the cage, an extended location away from the center of the cage sufficient to allow the staple tines of the staple head to further engage or embed themselves in the bone to mechanically engage and stabilize the staple head and the cage to the bone, or (3) for embodiments with a non-extendable staple within the cage, generally at the lateral location of the deployed position sufficient to allow the staple tines of the staple head to engage or embed themselves in the bone to mechanically engage and stabilize the staple head and the cage to the bone, or (4) for embodiments with a non-extendable staple outside of the cage, generally at the lateral location of the deployed position. With a first staple head in this stabilized position, a second staple and staple head may provide a counter force to the first staple head.

To support the above positions, the staple may comprise the staple head and a staple shaft. The staple shaft may be configured to move and rotate the staple head through the above positions relative to a longitudinal axis of the staple. The staple shaft may rotate about the staple longitudinal axis and the staple shaft may translate along the staple longitudinal axis. For example, the staple shaft may be rigidly coupled to the staple head and configured to move the staple head from an extended position to a deployed position by a rotation of the shaft and the staple head. As another example, the staple shaft may be configured to move the staple head from an insertion position to an extended position by moving the staple shaft through a bore of the cage and extending the staple head away from the cage along the longitudinal axis of the staple. The staple shaft may also be configured to move the staple head from a deployed position to a stabilization position by slidably moving the staple shaft through a bore of the cage and retracting the staple shaft and staple head towards the cage. The staple shaft may also be configured to move the staple head by a combination of translating and rotating the staple shaft.

To support the positioning and movement of the staple shaft and staple head through different alignments and longitudinal locations, a coupling mechanism may be provided. The coupling mechanism generally includes the implant system components that may be manipulated to move, or any combinations of features of implant system components that may influence the movement of, implant system components relative to each other. For example, the coupling mechanism may include implant system components configured to be engaged by one or more tool whereby the coupling mechanism moves the staple shaft and staple head through the different alignment and longitudinal locations described herein. The alignments are generally the rotational positions of the staple head and the longitudinal locations are generally the locations of the staple head as it translates relative to the cage.

The coupling mechanism may be configured to move the staple through the different longitudinal locations of the above positions. To support the movement of the staple head through the different longitudinal locations, the staple shaft may also be configured to translate to move the staple head by having the staple shaft mate with a coupling device to translate the staple head relative to the cage. For example, the staple shaft may have a coupling portion configured to be engaged by a coupling element to translate the staple shaft and staple head. For example only and not for limitation, the staple may be configured to move the staple head from an insertion to an extended lateral location by having a threaded staple shaft coupling portion configured to mate with a threaded coupling element whereby rotating the coupling element extends the staple head away from the cage. The staple shaft may also be configured to move the staple head from the deployed to a stabilization lateral location with the coupling portion and coupling element. For example, the staple may have a threaded shaft coupling portion configured to mate with a threaded coupling element whereby rotating the coupling mechanism retracts the staple head towards the cage.

In some embodiments, the coupling mechanism may also be configured to move the staple through the different alignment positions. The coupling mechanism may be configured to move the staple head by configuring the staple shaft to rotate the staple shaft and the staple head. For example, the coupling mechanism may also include a keyway mechanism to provide features that allow the coupling mechanism to allow and restrain movement of the staple shaft when the staple shaft is in different positions. The keyway mechanism may be any combination of elements or any combination of features of elements that can restrain the alignment or longitudinal locations of the staple in one position and can allow for alignment or longitudinal location changes in another position. For example, the keyway mechanism may allow the staple shaft to translate along its longitudinal locations without changing its alignment when the staple shaft is in one position and the keyway mechanism may also allow the staple shaft to move into another alignment without translation when the staple shaft is in another position.

In some embodiments, the coupling mechanism may also be configured to influence the movement of other implant device components. For example, the coupling mechanism may include an engagement mechanism to influence the movement of additional implant device components. The engagement mechanism may be any combination of elements or any combination of features of elements that allow one component of the coupling mechanism to move another implant device component. For example, the staple shaft may have an engagement portion that mates with an engagement portion on a second staple to allow the second staple to alter its alignment with the first staple.

In some embodiments, the one or more staple is positioned on one or more sides of the implant to be secured to the vertebral body yet control of the positioning of the staple is done by manipulating system elements and features accessible on another side of the implant. These features are particularly beneficial for vertebral procedures where the implants are inserted and secured from an anterior, anterior lateral or an oblique approach angle and the implant is implanted across the vertebral body and secured to both lateral sidewalls of the vertebrae. These procedures include the ATP approach to access the vertebral body and implant the implant device. These features may also be beneficial when the implant device is inserted and implanted through a posterior or posterior lateral approach trajectory to the vertebrae.

In some embodiments, components of the implant device may include lattice surface or wall configurations or other surface or wall configurations to encourage bone growth and secure the implant device to bone. For example only and not for limitation, the cage may be made with portions having lattice structures or it may have a percentage lattice volume such as about 40-70 percent.

The implant device may be manufactured from any suitable material including commercially pure titanium, titanium alloy, polyetheretherketone or any other appropriate material, even allogenic bone. In one example, all of the components of the implant device are made of a surgical grade metal such as Titanium (e.g., ASTM F136 Wrought 6Al4V Ti for Implant). The implant device components may be manufactured utilizing conventional machining technology (e.g., milling and turning, electro discharge machining, mass media and/or electropolish finishing, color anodizing, and passivation) or one of the several available methods additive manufacturing methods.

Example Embodiments of the Implant System:

It is understood that the disclosed implant systems and methods of use may be used with different orthopedic procedures including intravertebral, intervertebral and arthrodesis applications. For illustration purposes only, and not for limitation, an example of the implant system used for intravertebral applications will be described and referred to as a vertebral implant system, an intravertebral implant system, a vertebral implant device and an intravertebral implant device. In this illustrative example, the implant system comprises a vertebral implant device configured for use as an intravertebral implant device.

Although the example embodiments illustrate a multi-section cage, it is understood that the cage may be a unitary cage and the securing elements may be configured to translate relative to the cage.

Embodiments with External Securing Elements

For illustration purposes and not for limitation, one example of the vertebral implant device is shown in FIGS.

Figure 2A:
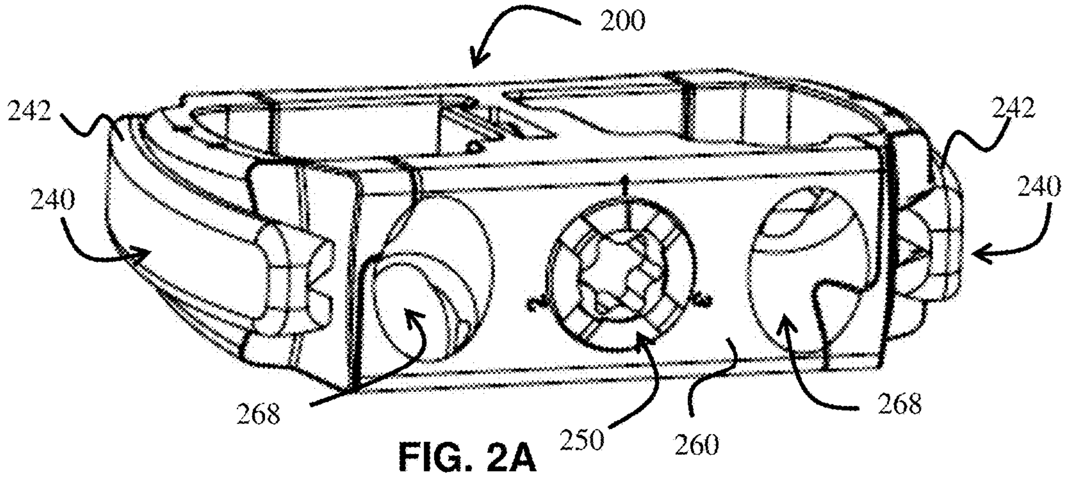
FIGS. 2A-2D show an example embodiment of an implant device with two staples.
Figure 2B:
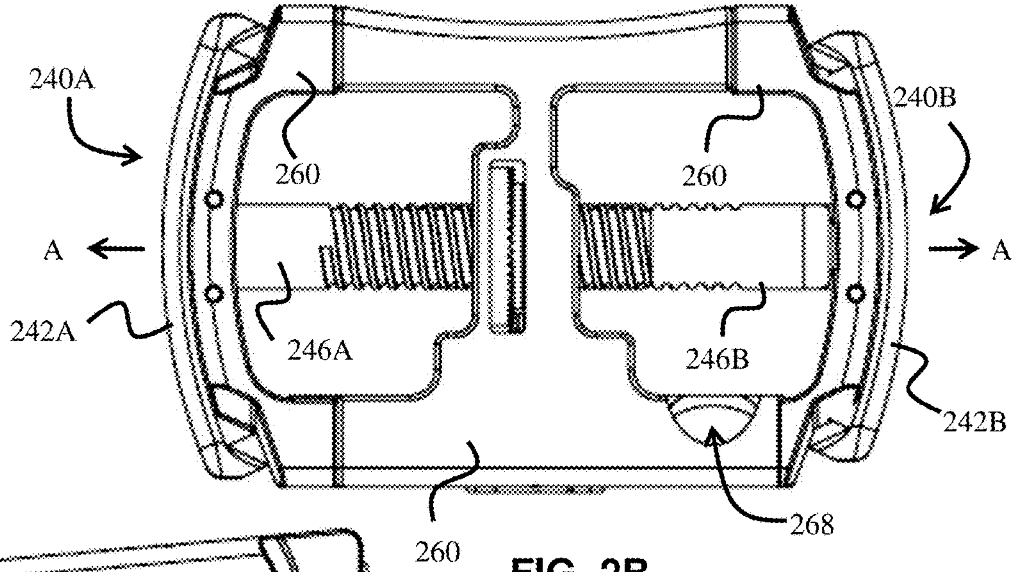
Figure 2C:
Figure 2D:
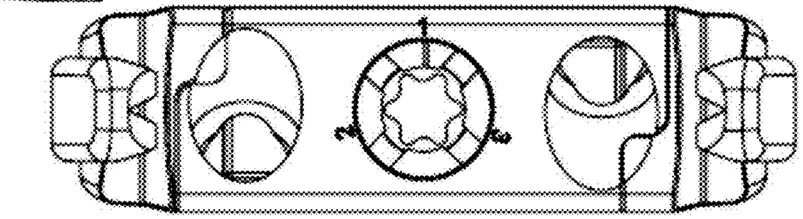

2A-2D. FIG. 2A shows a perspective view of the vertebral implant device, FIG. 2B shows a top view, FIG. 2C shows a side view and FIG. 2D shows a front view. In this example embodiment, the securing element positioned outside of the body of the cage.

As shown in the example of FIG. 2A, the vertebral implant system generally comprises a vertebral implant device 200 comprising a cage 260 and one or more securing element 240 configured to secure the cage 260 to the vertebral body. The cage 260 may be any suitable element to provide structural support between two bone portions such as between two vertebral bodies. The cage may have a top surface aligned at an angle to a bottom surface as shown in FIG. 2C. The cage 260 may have a proximal side, a distal side, two lateral sides and rounded edges between the side to assist in the placement of the cage 260. The cage 260 may be symmetrical or non-symmetrical. And the cage 260 may be a unitary structure or the cage 260 may have multiple sections. The securing element 240 may be any suitable element or combination of elements to secure the cage 260 and the implant device to a superior and inferior portion of the vertebral body. In the example shown, the securing element 240 may comprise one or more staple received in, and movable relative to the cage 260. The securing element 240 may have a head with a long axis, a short axis, rounded corners, and a convex shape whereby the ends of the securing element 240 bow in towards the cage. In the embodiment shown, the securing element 240 has one or more head outside of the walls of the cage. In some embodiments, the shape of the securing element may be any shape that allows the securing element 240 to be inserted and moved to a position where it engages the bone. For example only and not for limitation, the securing element shape may generally be rectangular, rounded rectangular, trapezoidal, square, oblong, oval, cylindrical or conical. The securing element 240 may be movable by rotation or translation relative to the cage 260. The securing element 240 may further comprise a head 242. The securing element 240 may further comprise a shaft 246A configured to allow another shaft 246B to overlap allowing two shafts to translate relative to each other. For example, see 246A and 246B in FIG. 2B which shows the shafts as overlapping mating half round shafts that allow the shaft 246A of securing element 240A and the shaft 246B or securing element 240B to translate in opposite directions. FIG. 2B also show staple heads 242A and 242B of each of the securing elements 240A and 240B. The securing element 240 is also generally configured to rotate about a staple rotation axis A extending generally longitudinally along the shafts 246A and 246B. In some embodiments, the vertebral implant device further comprises recesses 268 to receive one or more anchoring element (not shown) configured to anchor the implant system in the vertebral body. The anchoring element may be any suitable element or combination of elements to anchor the implant device to the vertebral body. The anchoring element may be one or more bone screw. As shown, the head 242 of the securing element 240 is configured to be positioned outside the boundaries of the vertebral body when implanted. For intravertebral applications, it is understood that the staple dimensions may be non-symmetrical to account for varied bone dimensions resulting from the osteotomy. The implant device may also comprise a coupling mechanism 250 configured to manipulate implant device components.

Figure 3A:
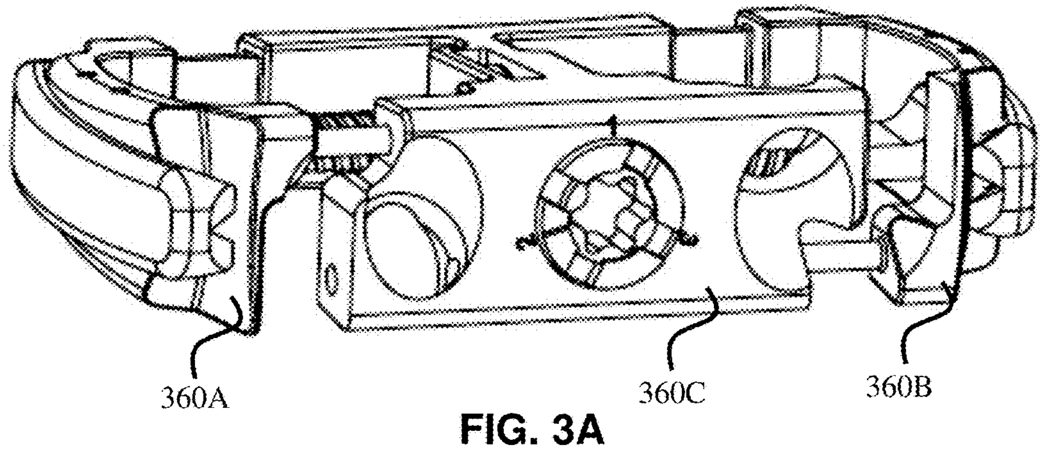
FIGS. 3A-3C show different views of the example embodiment of the vertebral implant device with the lateral sections of the cage extended.
Figure 3B:
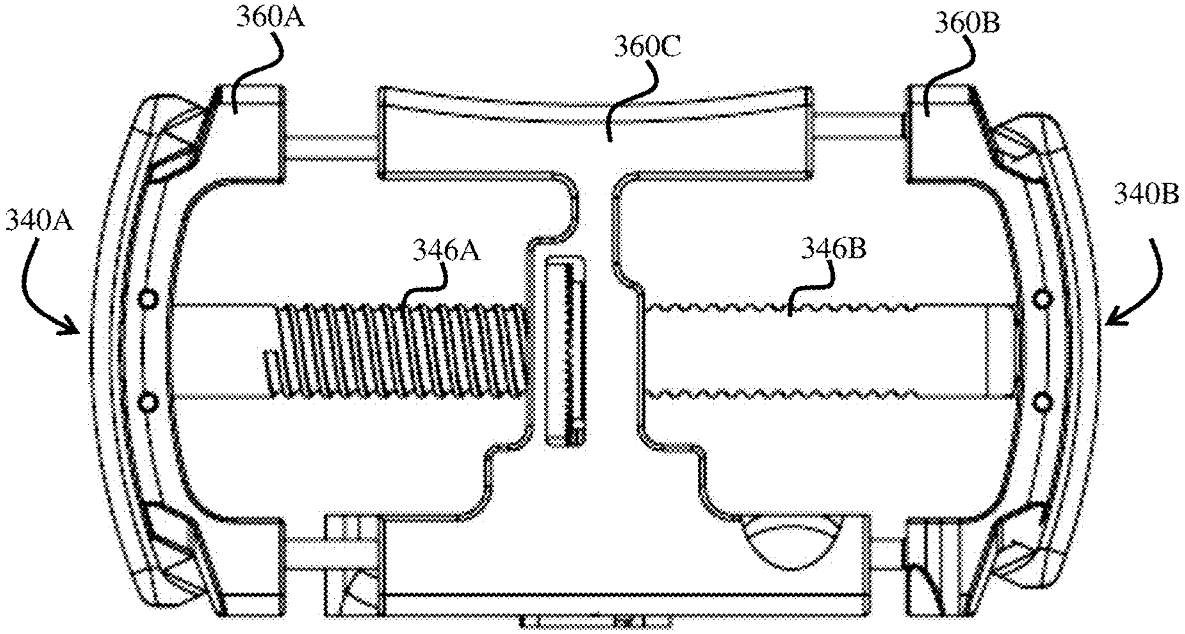
Figure 3C:
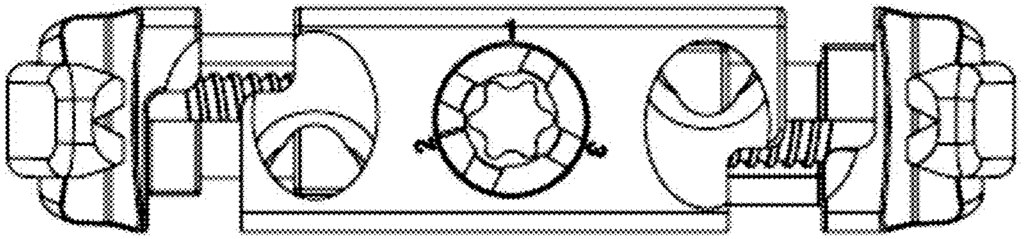

FIGS. 3A-3C show different views of the example embodiment of the vertebral implant device of FIGS. 2A-2D with a multi-section cage with the middle and lateral sections of the cage extended. FIG. 3A shows a perspective view of the implant device, FIG. 3B shows a top view, and FIG. 3C shows a front view. As shown, the cage is an extendable cage having a middle section 360C and two lateral sections 360A and 360B. As shown, the two lateral sections 360A and 360B are extended away from the middle section 360C. The lateral sections and the securing device, here staples 340A and 340B with staple heads, are coupled in a manner such that when the lateral sections extend, the corresponding staple and staple head are also extended away from the middle section 360C. For example, the staple shafts 346A and 346B may have a channel or a rib that mates with pins in the lateral sections of the cage to fix the position of the lateral sections 360A and 360B relative to the staple shafts 346A and 346B but still allow the staple shafts to rotate. By moving the lateral sections 360A and 360B, the staples 340A and 340B can be moved from an insertion position to an extended position. The staple shafts 346A and 346B allow each shaft to translate relative to the cage middle section 360C. For example, FIG. 3B shows the staple shafts 346A and 346B as half round shafts. This configuration of half-round shafts also functions as an engagement mechanism to allow the rotation of one staple shaft to rotate the other staple shaft. The positioning of the lateral sections 360A and 360B of the cage with the staple heads provide additional stability for the implant because the structural support of the lateral sections 360A and 360B will be positioned near the staple heads and therefore the sidewalls of the vertebral body when implanted.

Figure 4A:
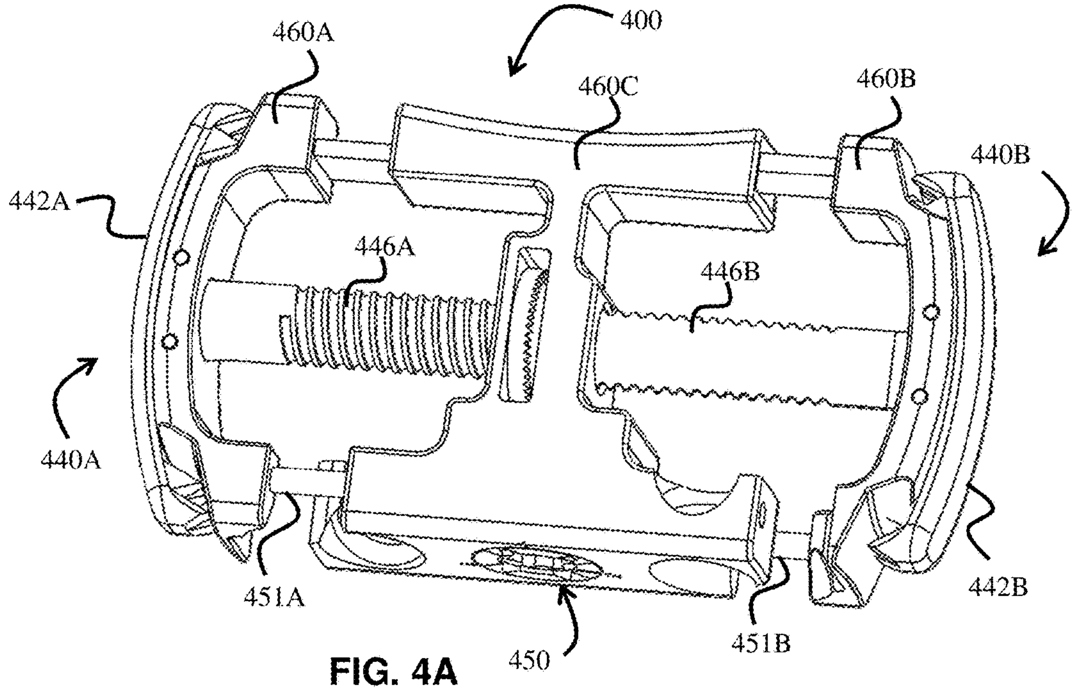
FIGS. 4A-4G show additional details of the vertebral implant device.
Figure 4B:
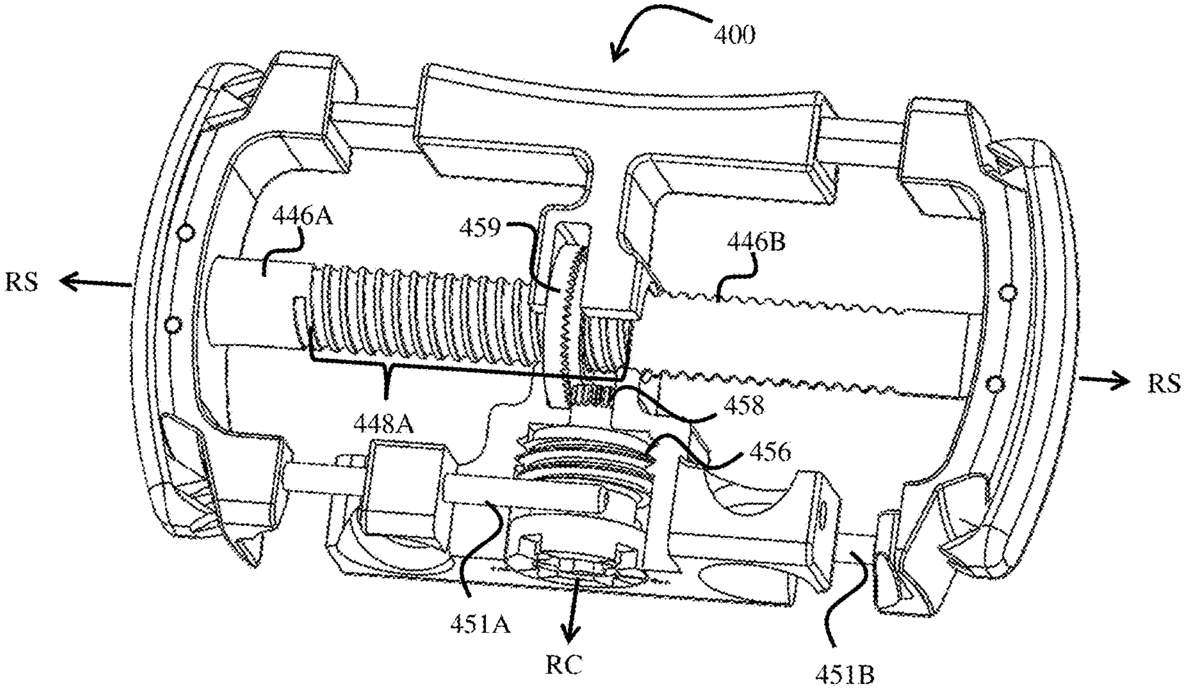

FIGS. 4A-4G show additional details of the example vertebral implant device 400. FIG. 4A shows a perspective view of the implant device 400 and FIG. 4B shows a cut-away view of the implant device 400 showing details of a coupling mechanism 450. The coupling mechanism 450 generally comprises the elements that manipulate the securing elements and the lateral cage sections. Referring to FIG. 4A, the coupling mechanism 450 generally provides a means to move the staples 440A and 440B and staple heads 442A and 442B relative to the cage. The coupling mechanism 450 may also provide a means to move the lateral cage sections 460A and 460B relative to the cage middle section 460C. The means to move may be a means to translate the securing element, such as staples and staple heads, and the lateral cage sections. The means to move may also be a means to rotate the staples and staple heads 442A and 442B. In the embodiment shown in FIG. 4B, the coupling mechanism generally comprises an inner nut 458, and outer nut 456 and a wheel 459. The inner nut 458 is nested in the outer nut 456 and both are able to rotate independent from each other. The nuts of the coupling mechanism 450 rotate about a coupling mechanism rotation axis. The wheel 459 is configured to engage the coupling portion of the staples whereby the wheel 459 manipulates the staples. For example and not for limitation, the wheel 459 may have a threaded center bore whose threads are configured to engage the threaded coupling portion of the staple shafts 446A and 446B. In this embodiment, the coupling portion is threads on the staple shafts, see coupling portion threads 448A on staple shaft 446A. The inner nut 458 is configured to engage the wheel 459. For example, the inner nut 458 has external teeth to engage external teeth on the wheel 459 so that when the inner nut 458 is rotated, it engages the teeth of the wheel 459 so that the wheel turns and the threaded center bore threads engage the staple shaft threads and the staple shafts translate relative to the wheel 459. The outer nut 456 is configured to engage pins 451A and 451B and prevent or restrain translation of the pins and therefore to prevent or restrain translation of the lateral cage sections. By preventing or otherwise restraining translation of the lateral cage section, a rotation of the inner nut 458 and a corresponding rotation of the wheel 459 rotates the staple shafts and the staples.

FIG. 4B also shows the general alignment of the coupling mechanism 450 in relation to the securing elements. As shown, the alignment of the coupling mechanism 450 allows rotation of the mechanism about a coupling mechanism rotation axis RC that is non-parallel with the rotation axis RS of the securing elements. In the embodiment show, the coupling mechanism rotates about the coupling mechanism rotation axis RC that generally runs from a proximal/anterior side of the implant device to the distal side of the implant device. The rotation axis RS of the securing elements generally runs along a longitudinal rotation axis that runs between the lateral sides of the implant device. This configuration of a non-parallel or transverse rotation axis RS compared to the coupling mechanism rotation axis RC allows the implant device 400 to be implanted and manipulated from an anterior approach trajectory to the patient and the spine while also allowing the securing elements to be positioned laterally. This lateral positioning of the securing elements is beneficial because it provides sufficient securing of the device while reducing the risk of impacting other body parts such as the spinal cord, nerve roots, surrounding musculature or posterior elements.

Figure 4C:
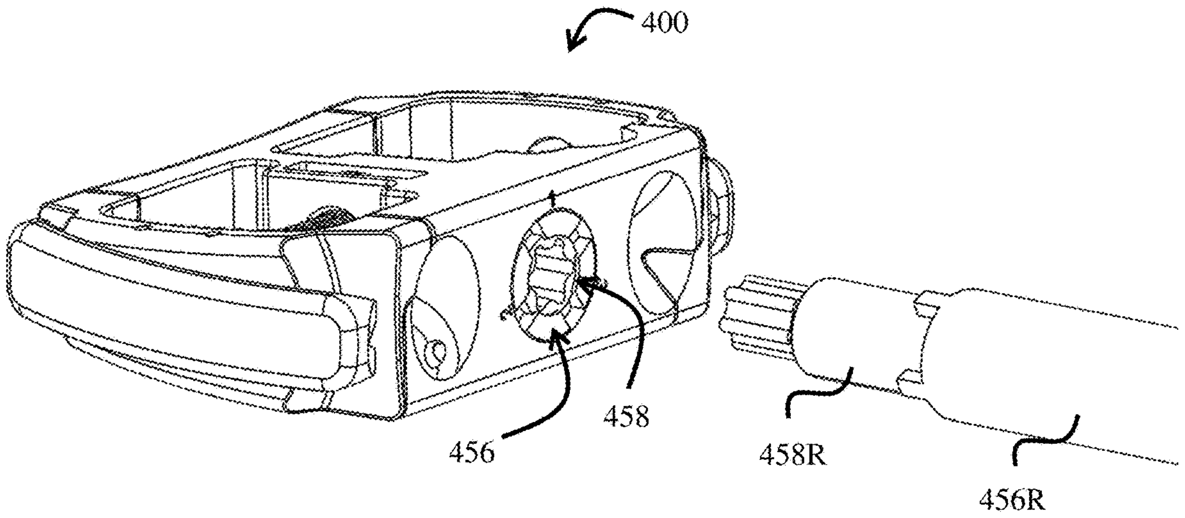
Figure 4D:
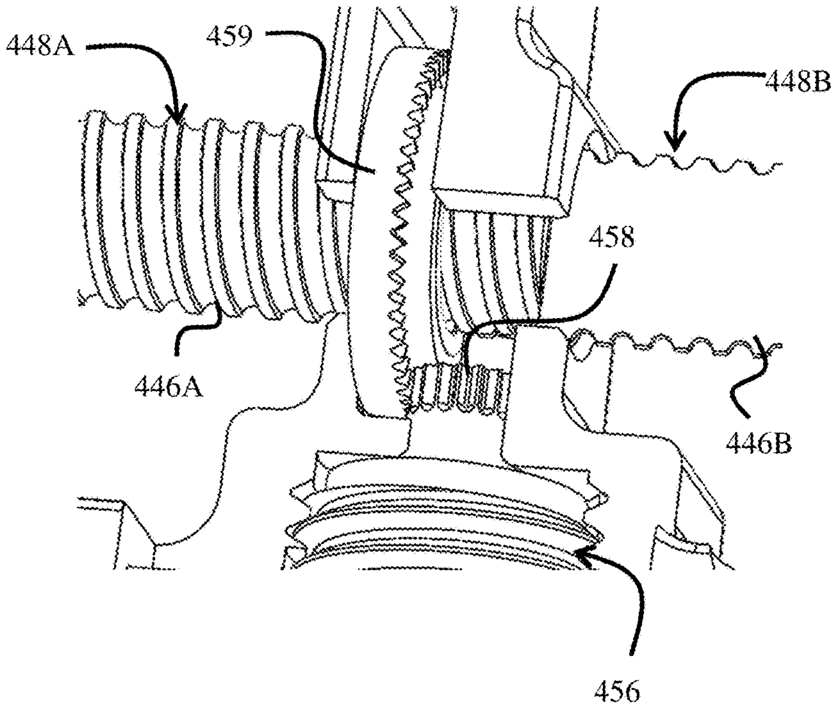

FIG. 4C shows the inner drive rod 458R and outer drive rod 456R of a staple drive handle assembly and illustrates how they engage the implant device 400. The drive rods are nested to allow the rotation of one drive rod while not rotating the other. The outer drive rod 456R is configured to engage an outer nut 456 in the proximal/anterior side of the cage and the inner drive rod 458R is configured to engage an inner nut 458 positioned rotationally within and extending through the outer nut 456. The outer nut 456 may be configured to lock the implant device in a series of positions by rotating the outer nut 456 with the outer drive rod 456R. The inner nut 458 may be configured to engage and translate and rotate the staple shafts and the staples. As shown in the example of FIG. 4D, the inner nut 458 engages the toothed wheel 459 which has threads inside its center bore to engage the outer threads 448A and 448B of the staple shafts 446A and 446B. Suitable staple drive handle assemblies may include those disclosed in and co-pending U.S. patent application Ser. No. 18/813,627 filed on Aug. 23, 2024, the entire disclosure of which is herein incorporated by reference.

Figure 4E:
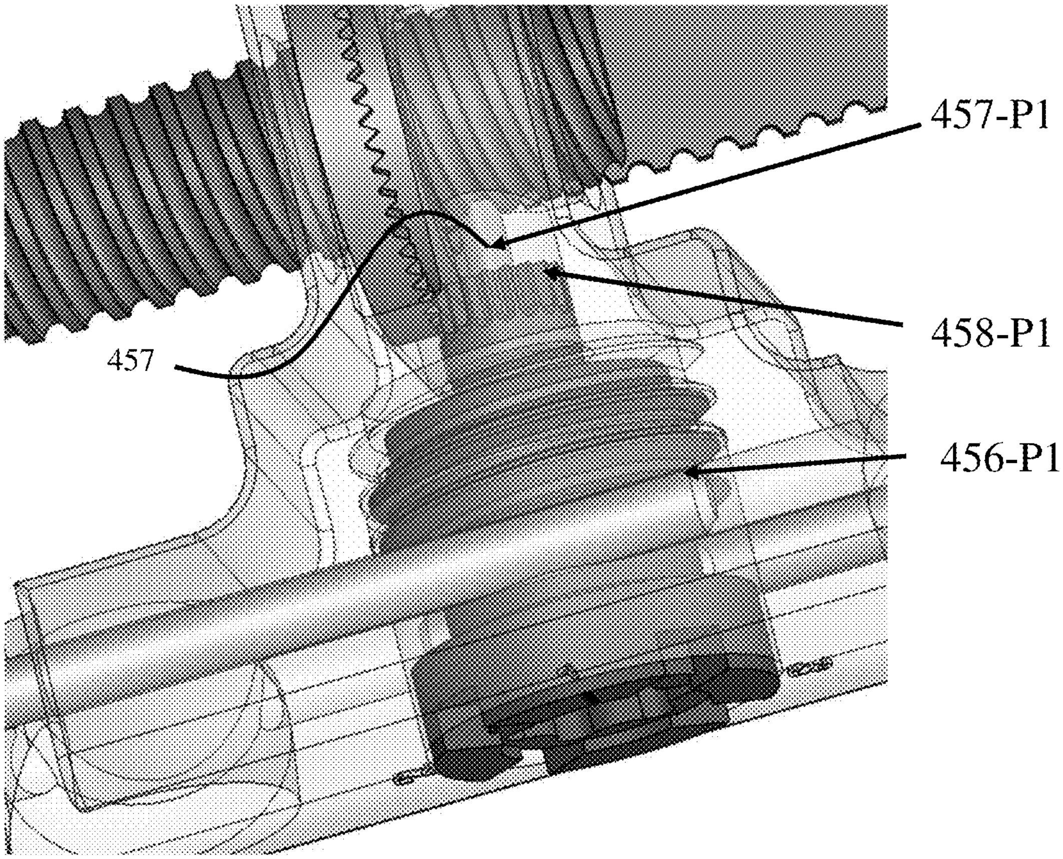
Figure 4F:
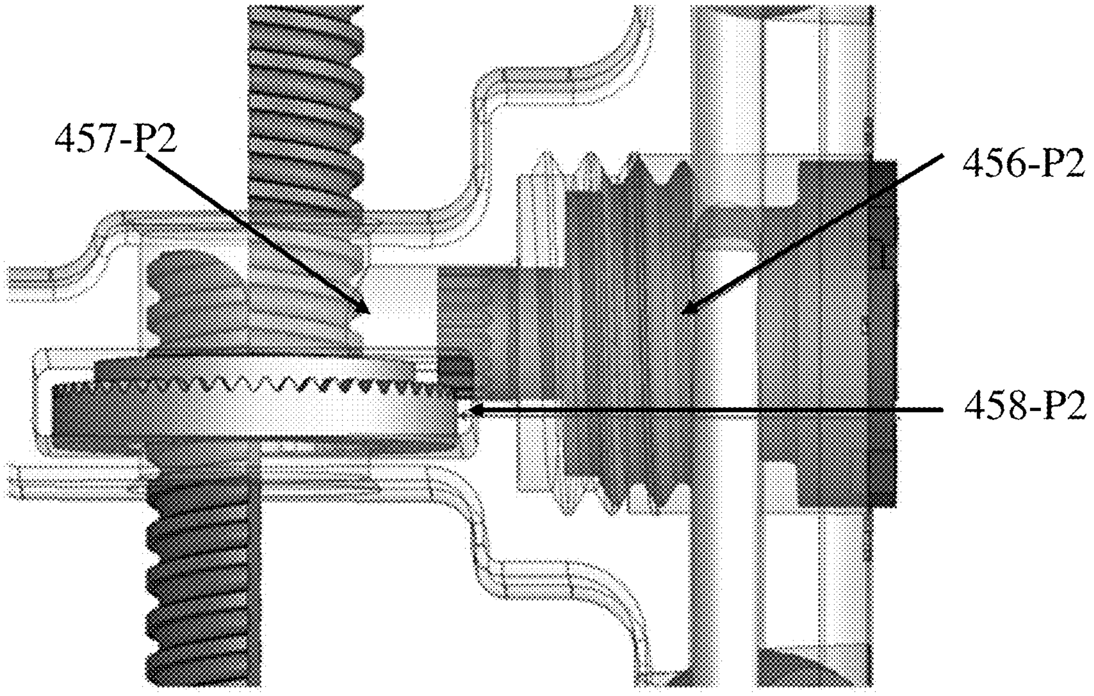
Figure 4G:
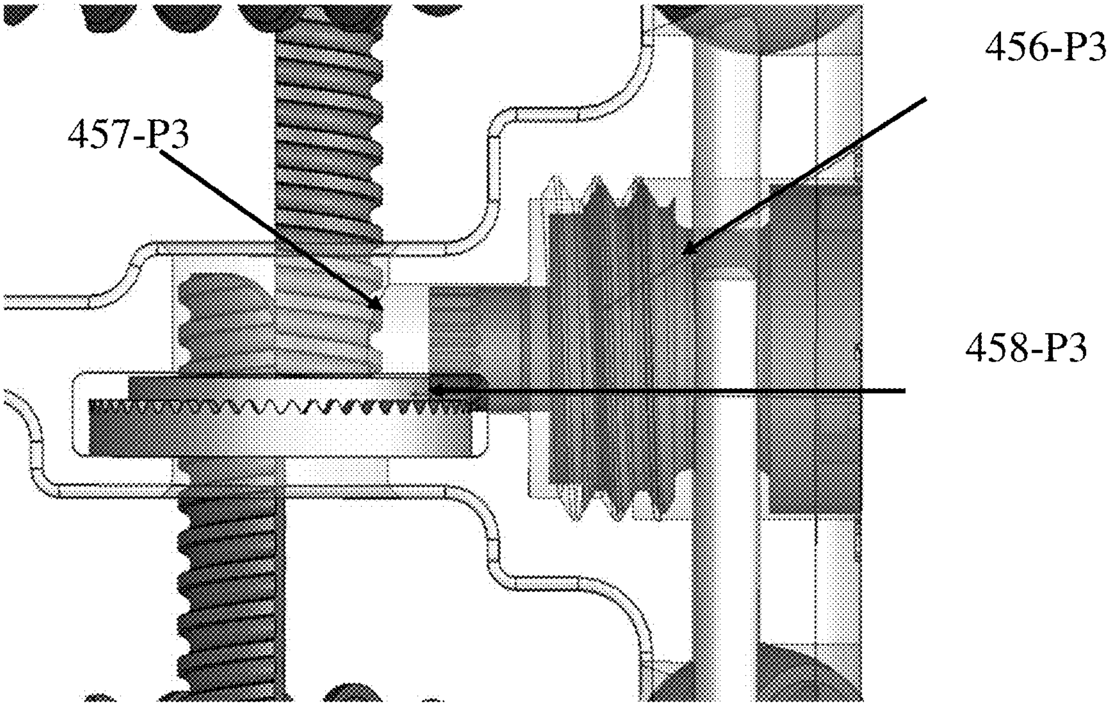

FIGS. 4E-4G show additional details of an example embodiment of the coupling mechanism and how it may be configured to engage the staple shafts and lateral sections of the cage. In this embodiment, the coupling mechanism and staple drive handle assembly are configured to enable the staple shafts and staples to (1) extend from an insertion position to an extended position, (2) rotate relative to the cage to a deployed position, and (3) retract towards the cage to a stabilized position and locked position. The coupling mechanism is configured to have multiple positions, generally by the in and out movement of the inner nut and the outer nut as manipulated by the inner and outer drive rods staple drive handle assembly.

FIG. 4E shows the staple shafts, the wheel, the pins, the inner nut, and the outer nut. This shows a position of the inner nut and the outer nut when the outer nut is rotated to a translation position 1. Translation position 1 puts a spring-loaded pin 457 in spring pin position 1, 457-P1, puts the inner nut in position 1 458-P1 and puts the outer nut in position 1 456-P1. This translation position 1 allows the staples to translate to the extended position without rotation. In this position, one of three positions for the outer nut, the outer nut is not jammed against the pins and this allows the later cage sections and the staples to translate. This also shows that the distal end of the inner nut is not jammed against the wheel so that the wheel can rotate with a rotation of the inner nut, and the threads of the wheel engage the staple shaft threads and the staples translate. As shown, a spring-loaded pin 457 may be positioned on the distal end of the coupling mechanism to fit into a gap between the two staple shafts whereby the staple shafts are prevented or restrained from rotating. If the staples are rotated and the spring-loaded pin 457 is not in the gap between the two staple shafts (see FIG. 4F), position 1 also allows the staples to translate from a deployed position to a stabilized position. In this later position, the of the spring-loaded pin 457 is not sufficient to stop the staple shafts from translating.

FIG. 4F shows the staple shafts, the wheel, the pins, the inner nut, and the outer nut with the outer nut in another position. This shows a position of the inner nut and the outer nut when the outer nut is rotated to a rotation position 2. Rotation position 2 puts the spring pin in position 2, 457-P2, puts the inner nut in position 2, 458-P2, and puts the outer nut in position 2, 456-P2. This rotation position 2 allows the staples to rotate to the deployed position. In this position, the outer nut is rotated so that the threads of the outer nut are jammed against the guide pin preventing or restraining translation of the staples and the guide pins. The inner nut is positioned so that its distal end is not jammed against the wheel allowing the wheel to rotate when the inner nut is rotated. The spring-loaded pin may be retracted from the gap between the two staple shafts whereby the staple shafts are permitted to rotate. When the wheel is rotated, since the guide pins prevent or restrain the staples and staple shafts from translating, the inner nut rotates the wheel and this rotates the staple shafts and the staples. As shown, the movement of the coupling mechanism proximally pulls the spring-loaded pin out of the gap between the two staple shafts whereby the staple shafts can rotate.

FIG. 4G shows the staple shafts, the wheel, the pins, the inner nut, and the outer nut with the outer nut in another position. This shows a position of the inner nut and the outer nut when the outer nut is rotated to a locked or stabilized position 3. Stabilized position 3 puts the spring pin in position 3, 457-P3, puts the inner nut in position 3, 458-P3, and puts the outer nut in position 3, 456-P3. This stabilized position 3 moves the staples into a stabilized and locked position whereby the staples are prevented or restrained from rotating or translating. In this position, the outer nut is rotated to advance the inner nut and the outer nut. The outer nut is jammed against the guide pins preventing or restraining translation of the guide pins and the staple shafts and the inner nut is jammed against the wheel preventing or restraining it from rotation. As shown, the movement of the coupling mechanism also distally translates the spring-loaded pin against the staple shafts. The spring-loaded pin may be pushed against the staple shafts but the spring allows the spring-loaded pin to retract and permits the inner nut and the outer nut to translate to the stabilized position 3.

Figure 5A:
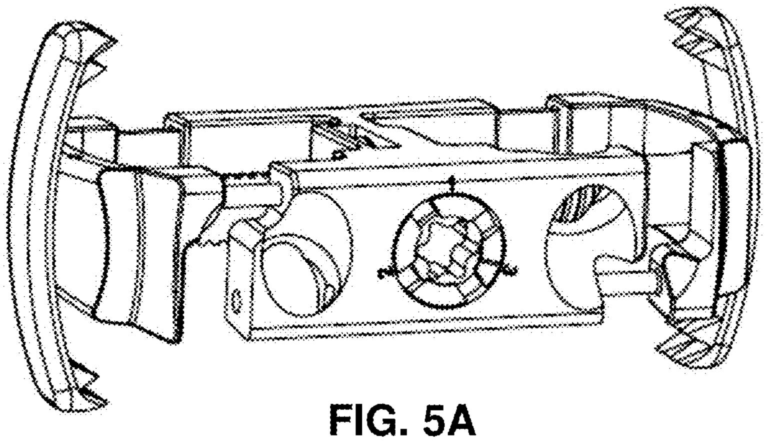
FIGS. 5A-5C show different views of the implant device with the staples in an example of a deployed position.
Figure 5B:
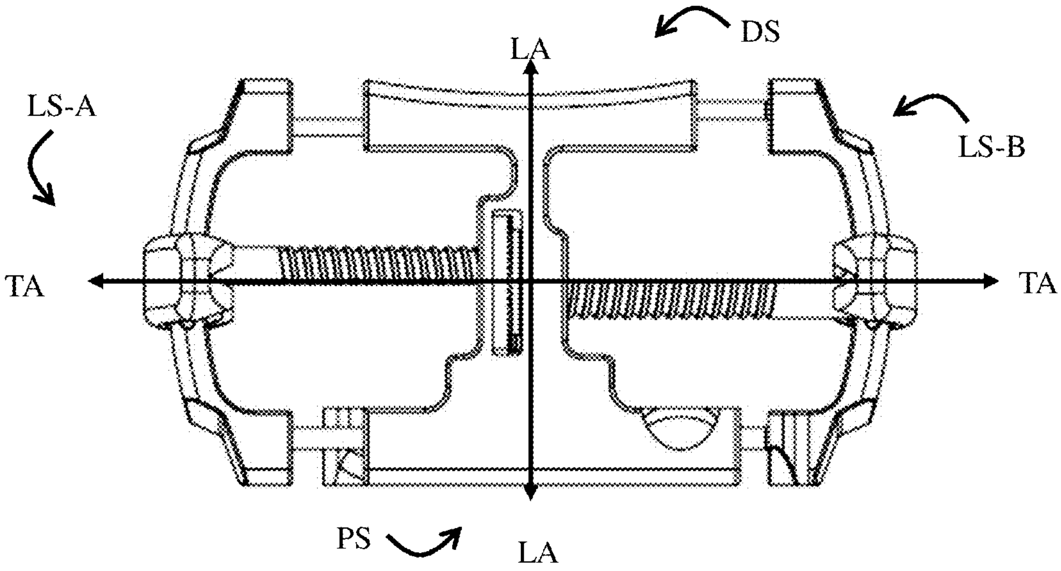
Figure 5C:
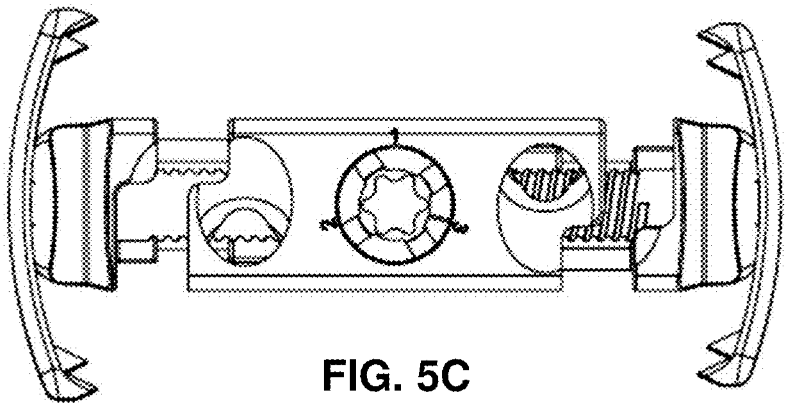

FIGS. 5A-5C show different views of the implant device with the staples in a deployed position. FIG. 5A shows a perspective view, FIG. 5B shows a top view and FIG. 5C shows a front view. FIG. 5B also illustrates a longitudinal axis LA of the cage extending from a proximal side PS to a distal side DS and a transverse axis TA extending from a first lateral side LS-A to a second lateral side LS-B.

Figure 6A:
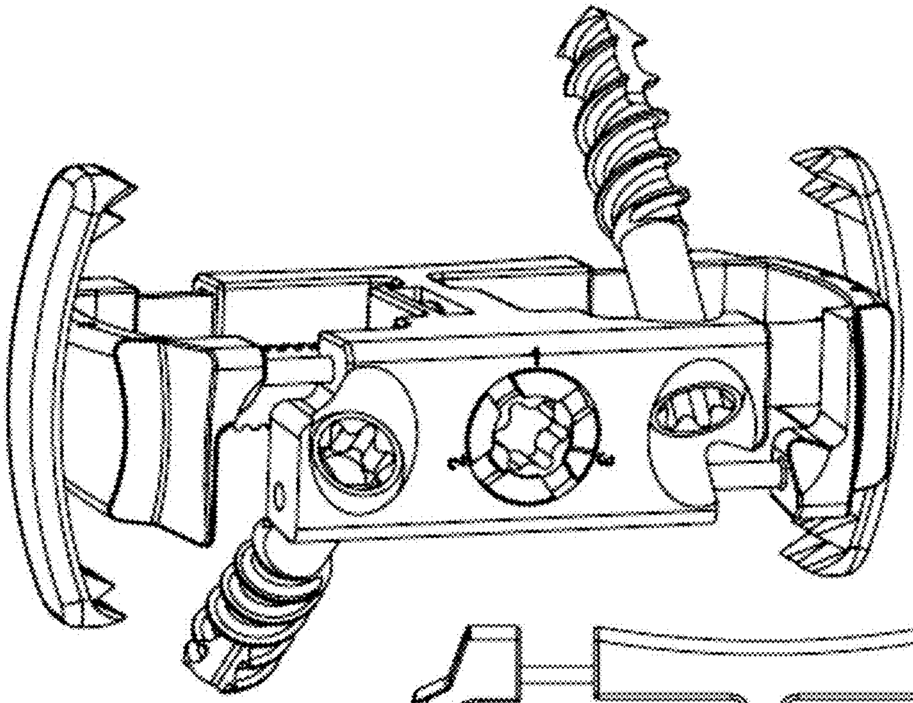
FIG. 6A-6C show different views of the implant device with the staples and anchor elements as the implant device may configured when in a stabilized position.
Figure 6B:
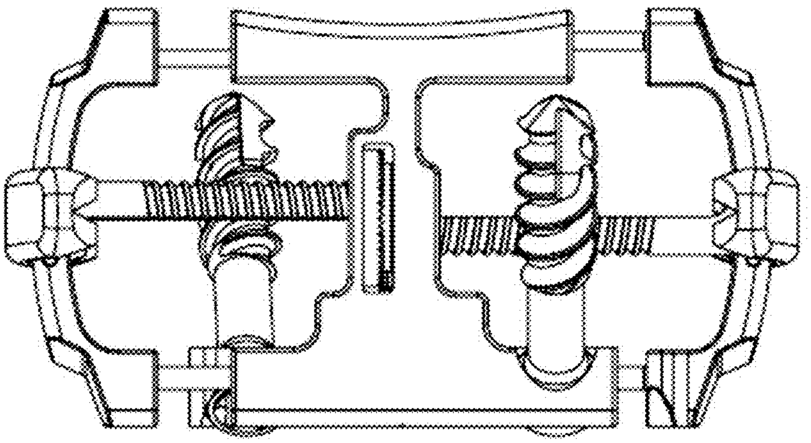
Figure 6C:
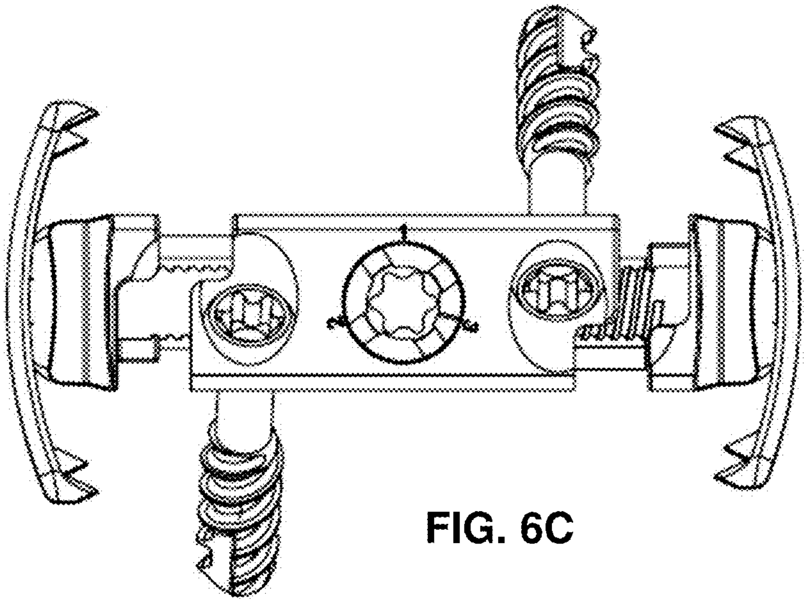

FIG. 6A-6C show different views of the implant device with the staples and anchor elements as the implant device may configured in a stabilized position. FIG. 6A shows a perspective view, FIG. 6B shows a top view and FIG. 6C shows a front view. For embodiments with two extendable staples positioned outside of the cage, in the stabilized position the relative positioning of the first staple and the second staple in the stabilized position is at a shorter distance than the relative position of the first staple and the second staple in the deployed position.

Figure 7:
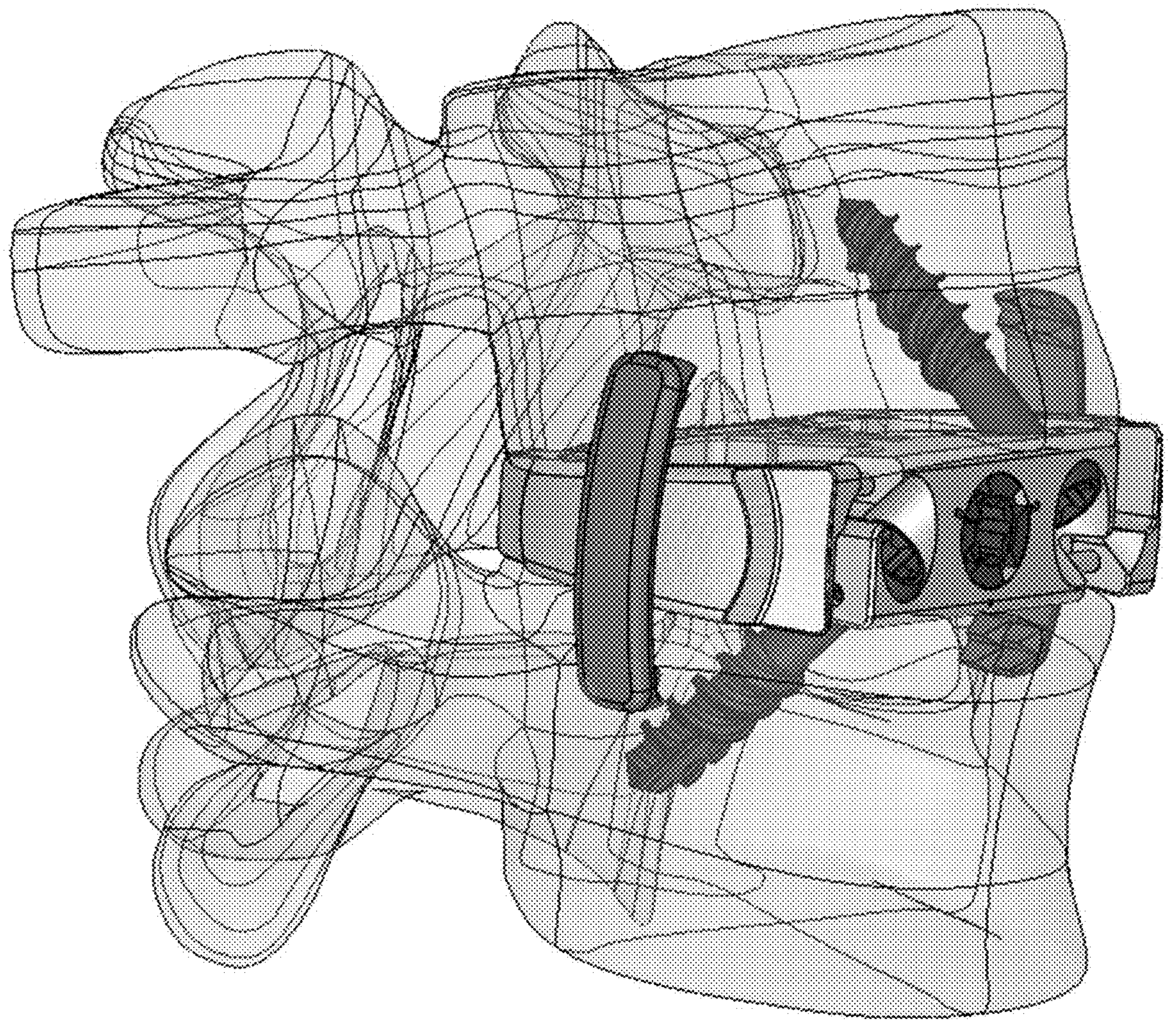
FIG. 7 shows a view of the implant device with the staples in the stabilized position and the implant device further secured to the bone with two bone screws.

FIG. 7 shows a view of the implant device with the staples in the stabilized position and the implant device further secured to two vertebral bodies with two bone screws after an intervertebral procedure. After an intravertebral procedure, the implant device and staples would be similarly positioned in the osteotomy space between an upper portion and a lower portion of the vertebral body.

Embodiments with Internal Securing Elements

Figure 8A:
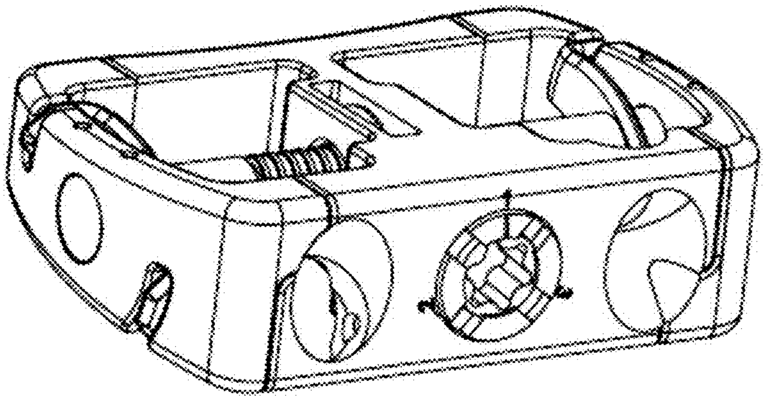
FIGS. 8A-8D show another example embodiment of the implant device.
Figure 8B:
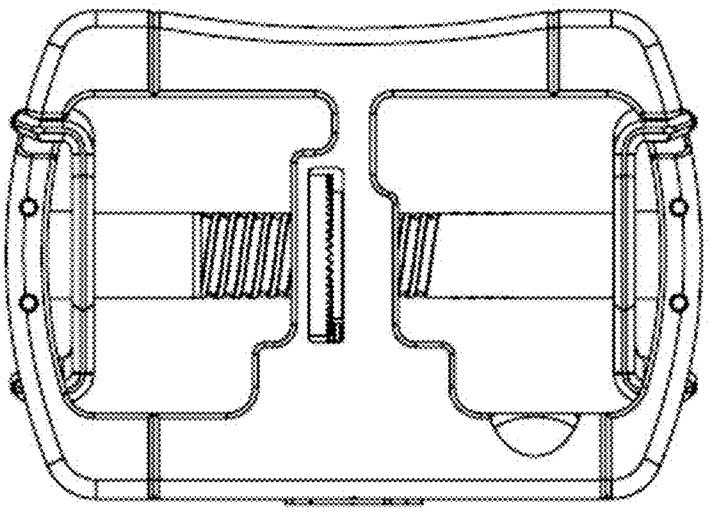
Figure 8C:
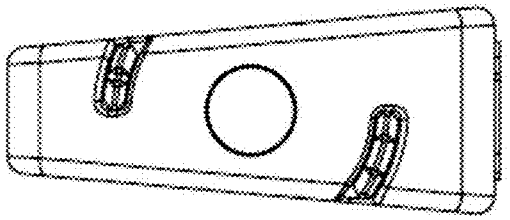
Figure 8D:
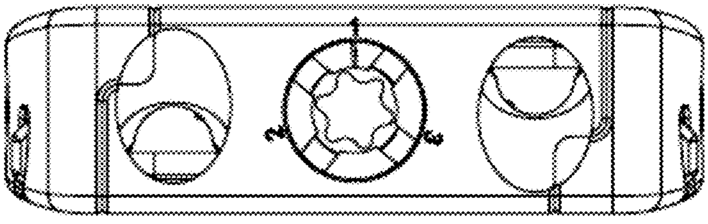

FIGS. 8A-8D show another example embodiment of the implant device with the securing element generally positioned within the cage. FIG. 8A shows a top perspective view of this example embodiment, FIG. 8B shows a top view, FIG. 8C shows a side view, and FIG. 8D shows a front view.

Referring to FIG. 8A, in this embodiment, the securing element is generally positioned within the implant cage and configured for intraosseous deployment. In this example embodiment, the securing element is one or more staple with the staple, staple head and staple tines configured to be stiff with the staple tines sharpened to penetrate vertebral bone. In this example embodiment, the staples are positioned in the lateral cage sections. In this embodiment, the staples can be rotated into the deployed position and extended away from the middle of the cage to further secure them in their stabilized position. The coupling mechanism may operate with the drive rods, the staple shafts, and the cage similar to the other embodiments described herein.

Figure 9A:
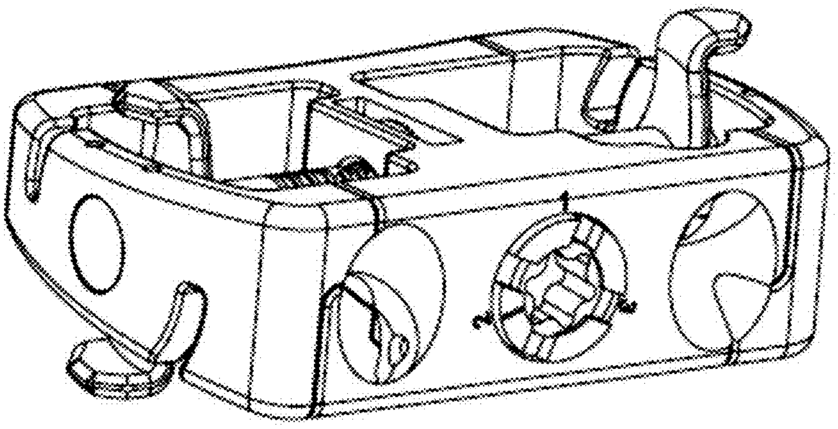
FIGS. 9A-9C show different views of the implant device with the staples in an example of a stabilized position.
Figure 9B:
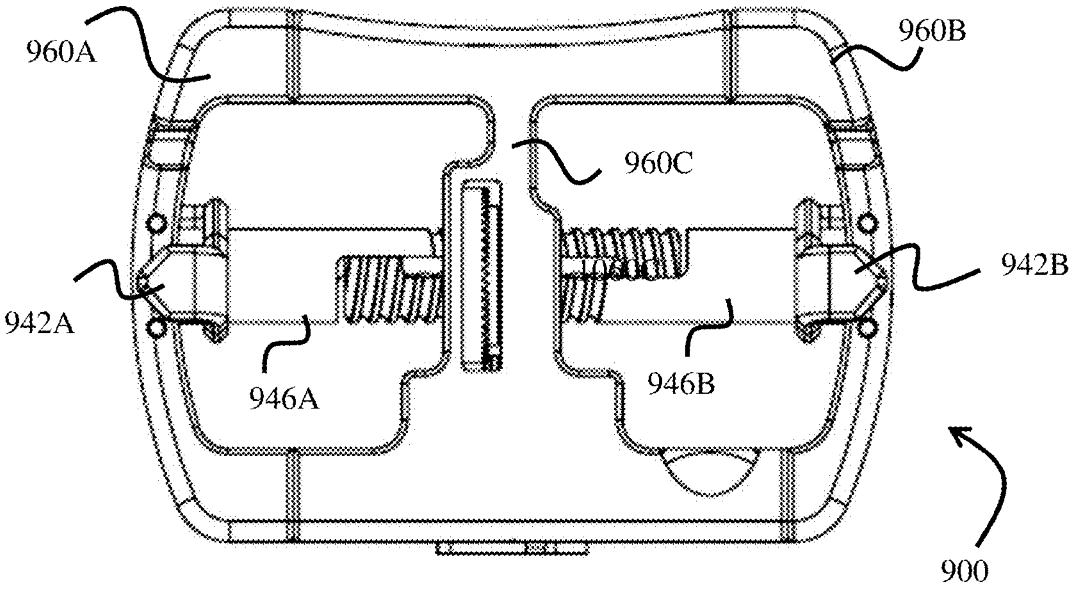
Figure 9C:
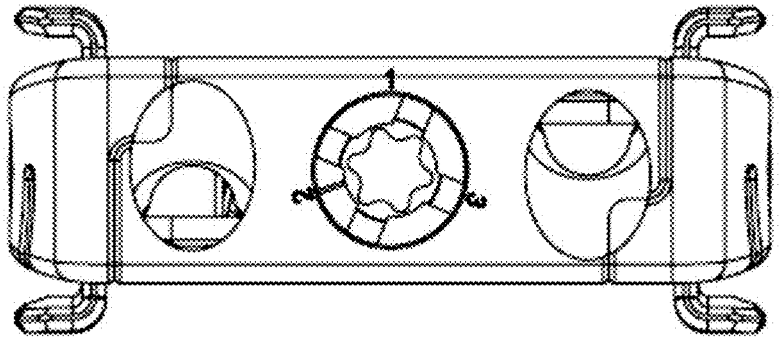

FIGS. 9A-9C show different views of the implant device with the staples in a stabilized position. FIG. 9A shows a perspective view of this example embodiment, FIG. 9B shows a top view and FIG. 9C shows a front view.

Referring to FIG. 9B, the vertebral implant device 900 is a multi-section cage with a middle section 960C, and extendable lateral sections 960A and 960B. The lateral sections 960A and 960B and the securing device, here staples with staple heads 942A and 942B, are coupled in a manner such that when the lateral sections 960A and 960B extend, the corresponding staple head 942A and 942B is also extended away from the middle section 960C. For example, the staple shafts 946A and 946B may have a channel or a rib that mates with pins in the lateral sections 960A and 960B to fix the position of the lateral sections 960A and 960B relative to the staple shafts 946A and 946B but still allow the staple shafts to rotate. By moving the lateral sections 960A and 960B, the staples heads 942A and 942B can be moved from an insertion position to an extended position. The staple shafts 946A and 946B allow each shaft to translate relative to the cage middle section 960C. For example, FIG. 9B shows the staple shafts 946A and 946B as half round shafts. The positioning of the lateral sections 960A and 960B of the cage with the staple heads 942A and 942B provide additional stability for the implant because the structural support of the lateral sections 960A and 960B will be positioned near the staple heads 942A and 942B and therefore the sidewalls of the vertebral body when implanted.

Figure 10A:
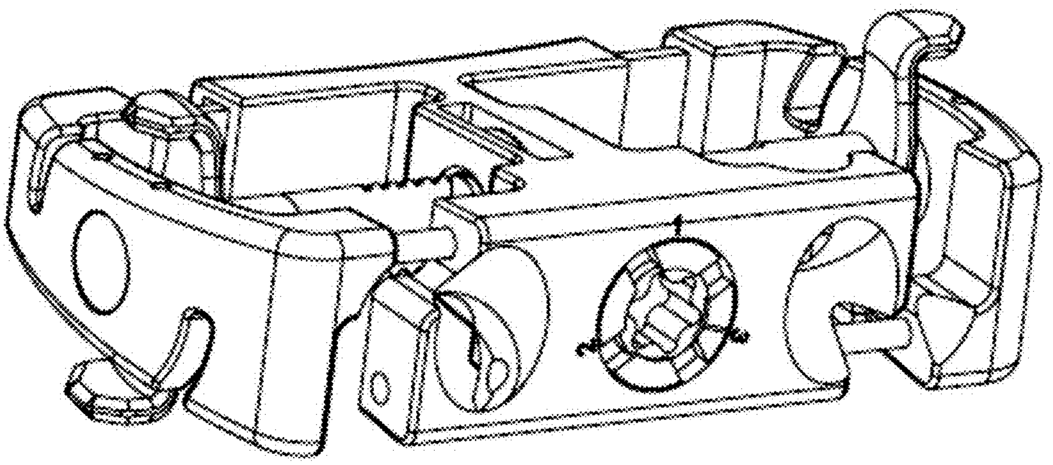
FIGS. 10A-10C show different views of the implant device with the staples in an example of a deployed position.
Figure 10B:
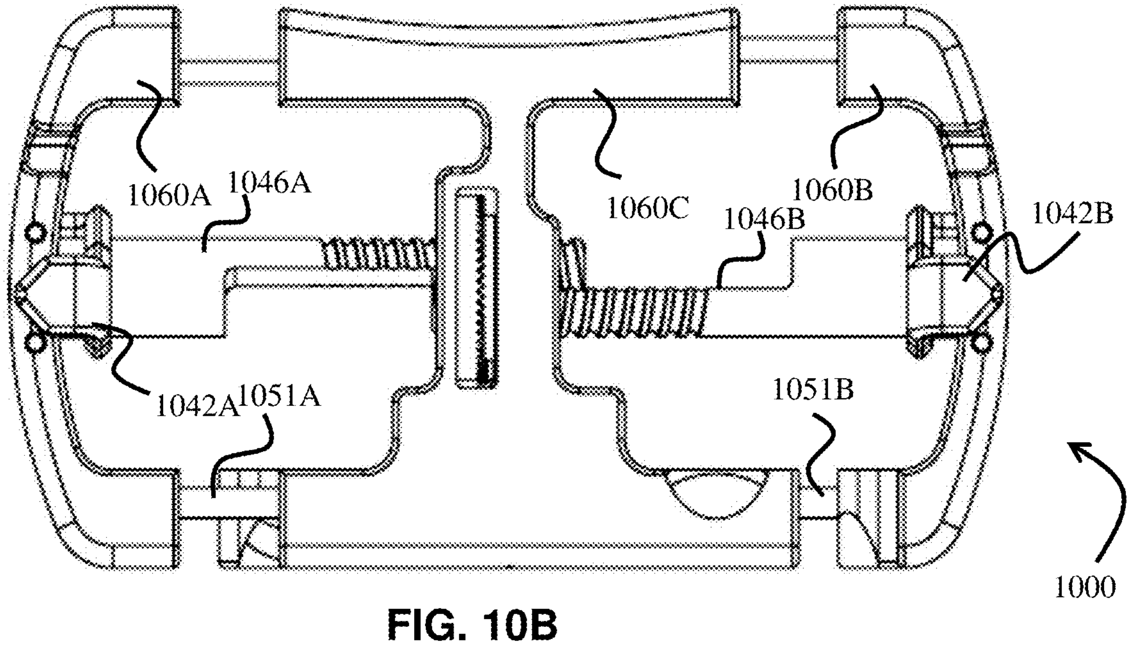
Figure 10C:
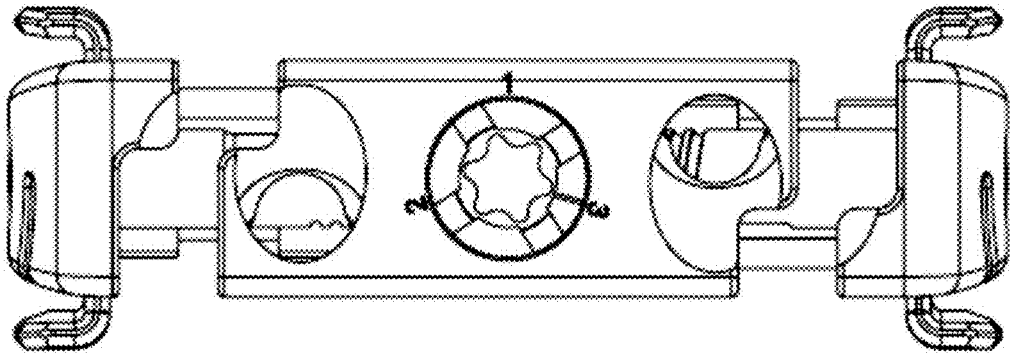

FIGS. 10A-10C show different views of the implant device with the staples in a deployed position. FIG. 10A shows a perspective view, FIG. 10B shows a top view and FIG. 10C shows a front view. In this embodiment, the staple shafts and stables are manipulated by staple drive handle assembly engaging the coupling mechanism. In this embodiment, the coupling mechanism and staple drive handle assembly are configured to enable the staple shafts and staples to (1) rotate from an insertion position to a deployed position, (2) extend away from the center of the cage to a stabilized position, and (3) lock in a locked position.

Referring to FIG. 10B, the cage is an extendable cage having a middle section 1060C and two lateral sections 1060A and 1060B. As shown, the two lateral cage sections 1060A and 1060B are extended away from the middle section 1060C. Staple heads 1042A and 1042B translate with the lateral cage section 1060A and 1060B, respectively. The staple shafts 1046A and 1046B are half rounds that allow each shaft to translate relative to the cage. The positioning of the lateral cage sections 1060A and 1060B with their respective staple heads 1042A and 1042B provide additional stability for this implant device 1000 because the structural support of the lateral sections will be positioned near the staples and therefore near the sidewalls of the vertebral body when implanted. This embodiment also shows pins 1051A and 1051B that are engaged by the coupling mechanism in the movement of the staples.

For embodiments with two extendable staples positioned inside the cage, in the stabilized position the relative positioning of the first staple and the second staple in the stabilized position is at a greater distance than the relative position of the first staple and the second staple in the deployed position.

Figure 11A:
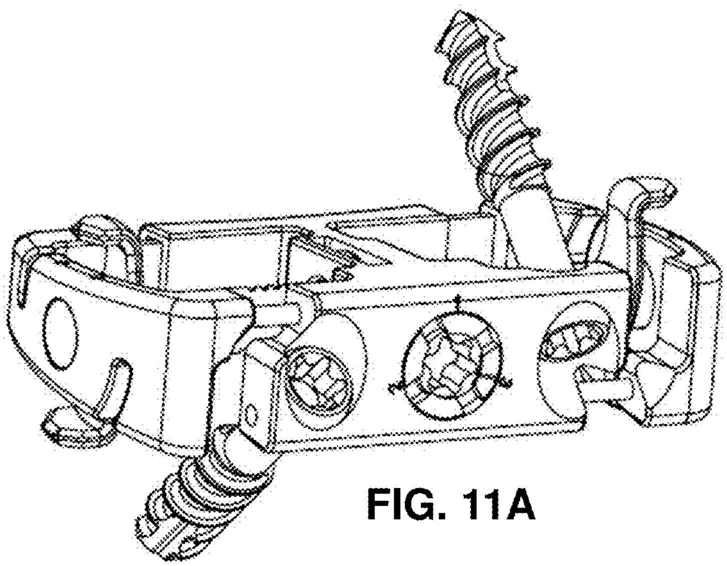
FIGS. 11A-11C show different views of the implant device with the staples and anchor elements as the implant device may configured when in a stabilized position.
Figure 11B:
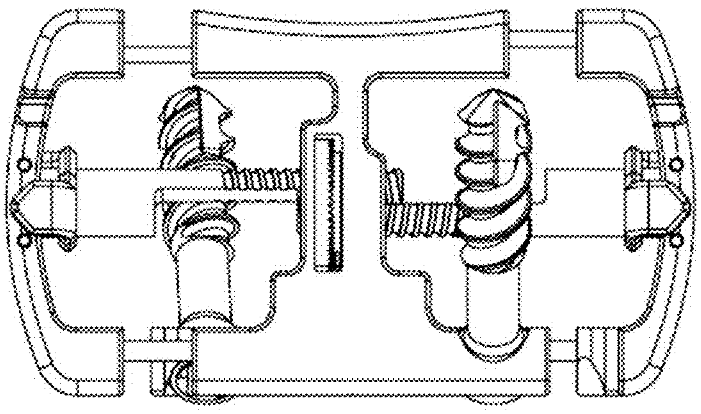
Figure 11C:
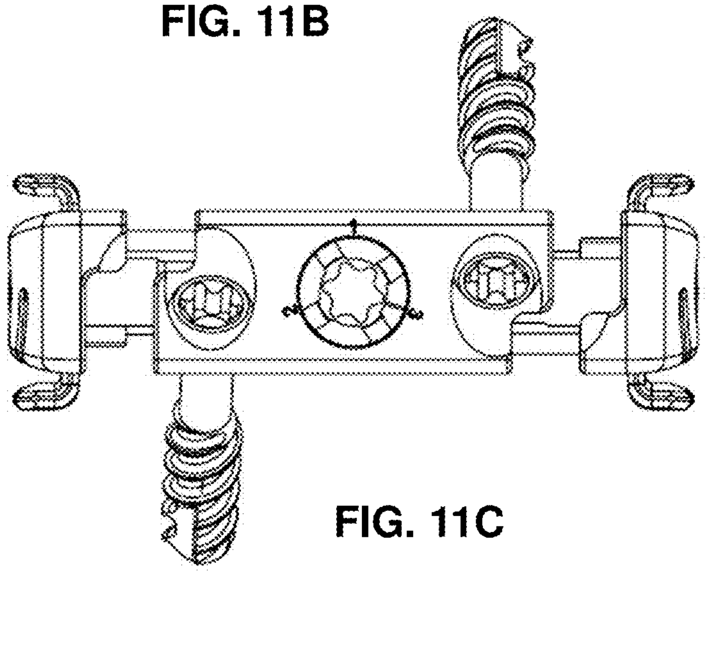

FIGS. 11A-11C show different views of the implant device with the staples and anchor elements as the implant device may configured when in a stabilized position. FIG. 11A shows a perspective view, FIG. 11B shows a top view and FIG. 11C shows a front view.

Figure 12:
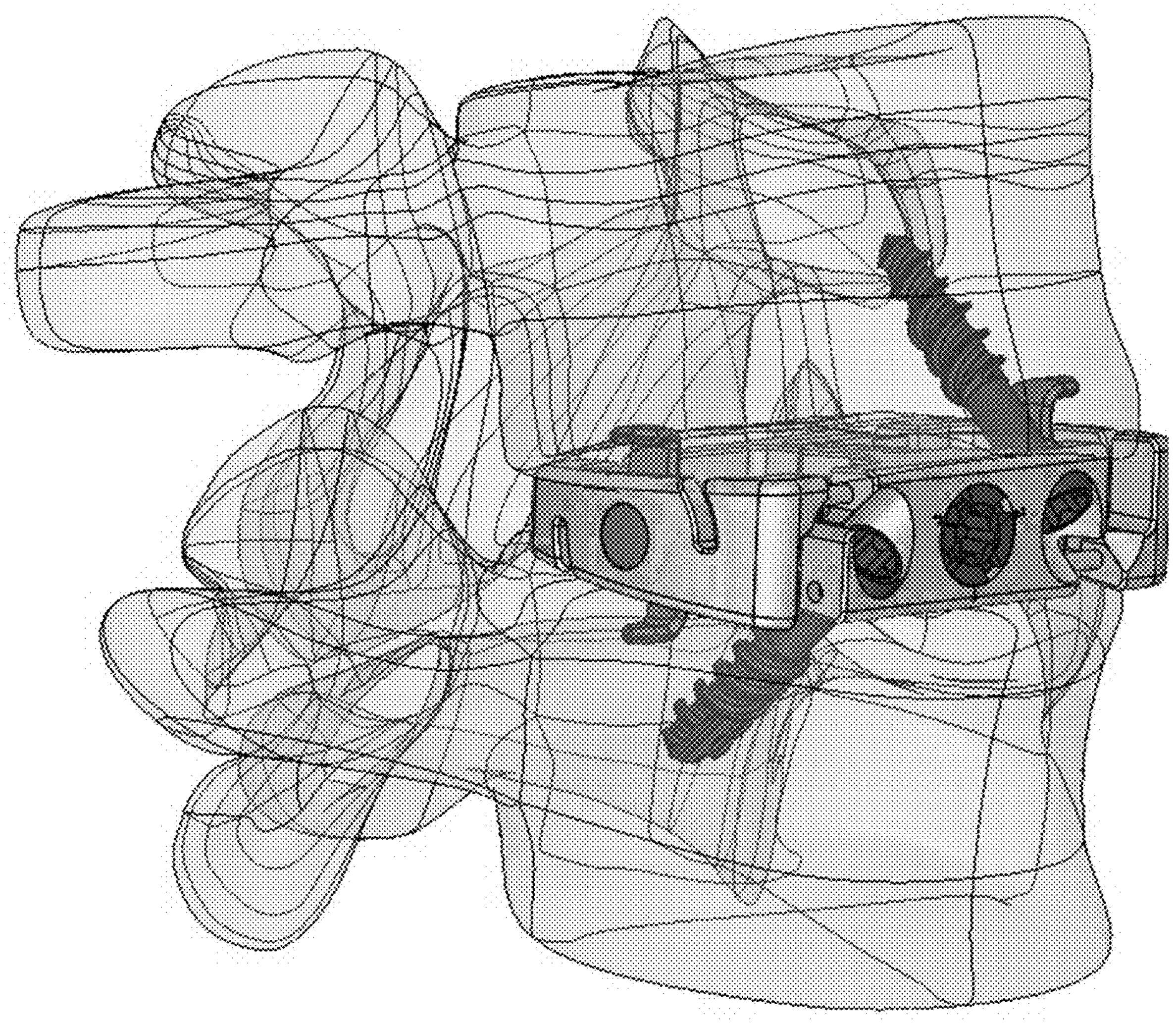
FIG. 12 shows a view of the implant device with the staples in the stabilized position and the implant device further secured to the bone with two bone screws.

FIG. 12 shows a view of the implant device with the staples in the stabilized position and the implant device further secured to two vertebral bodies with two bone screws after an intervertebral procedure. After an intravertebral procedure, the implant device and staples would be similarly positioned in the osteotomy space between an upper portion and a lower portion of the vertebral body.

Tools for Use with the Implant System

Figure 13A:
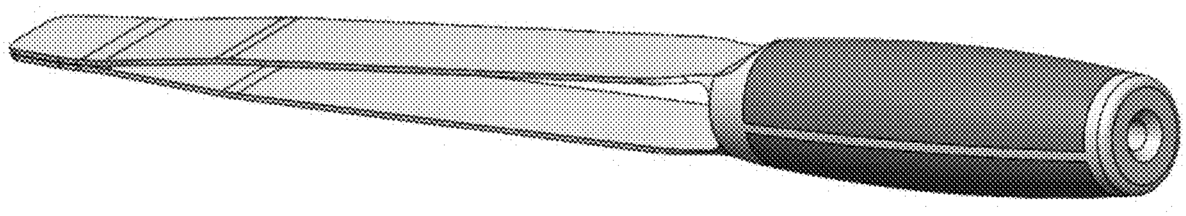
FIGS. 13A and 13B illustrate example embodiments of tools used to implant the implant device.
Figure 13B:
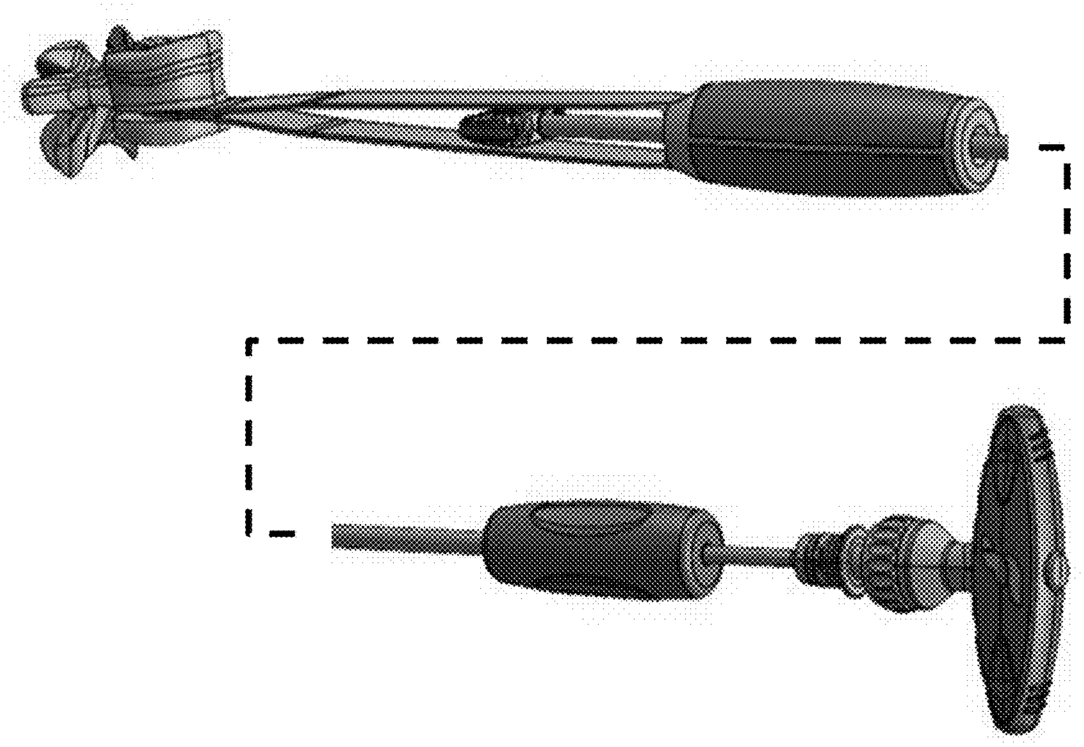

FIGS. 13A and 13B show example embodiments of tools that may be used in the insertion of the implant device. FIG. 13A shows an example implant insertion channel guide. The implant insertion channel guide may have two prongs between which the vertebral implant device is positioned. The vertebral implant device may be placed on the end of a staple drive handle assembly received in the insertion channel guide whereby the vertebral implant device may be manipulated at a distal end of the insertion channel guide by manipulating a proximal end of staple drive handle assembly.

As described above, a staple drive handle assembly may also be used. FIG. 13B shows a broken view of a staple drive handle assembly. Consistent with the embodiment shown in FIG. 4C, the staple drive handle assembly may have nested inner and outer drive rods, each coupled to a handle that allows the separate rotation of each rod.

Additional Features

In some embodiments, the cage may have a surface treatment or a lattice configuration on one of or both the upper surface of the lower surface as well as on interior surfaces to encourage bone growth, apposition, and/or adhesion.

In some embodiments, the external surface configuration of the cage and the vertebral implant device may be altered by using different configurations of vertebral implant device components. For example, the cage may be configured to have different cage surface angles in either the coronal or sagittal planes to create different external surface configuration when implanted in the osteotomy. The cage may also be configured to have different heights to create different amounts of expansion when implanted in the osteotomy. Sets of multiple exchangeable cage configurations can provide implant device options to accommodate different vertebrae, different sized patients, different amounts of correction and different orientations of insertion.

In some embodiments of the implant system may be configured to alter the alignment of the spine in multiple planes. This multi-plane alignment may be made by the insertion angle of the implant and/or the dimensions of the cage and the resulting cage surface angles.

In some embodiments, additional through-holes may be provided in the anchor frame and/or the cage and/or the securing element to accommodate additional pedicle screws to further anchor the implant device to the vertebral body. In these embodiments, the pedicle screw may be received in the additional through-holes and into the vertebral body.

In some embodiments, the cage may be filled with bone graft material of choice prior to implanting. During this step, the staple is in an insertion position to pass through the osteotomy site with the cage. With the cage in place, the implant insertion channel guide can then be removed.

In some embodiments that use cage screws, the cage screws may incorporate an anti-backout thread design (e.g., spiral-lock) or anti-backout elements to prevent loosening or disengagement of the cage from the anchor frame once it is implanted.

In some embodiments, a bone screw anti-backout feature may be positioned over the heads of the bone screws to prevent them from backing out.

In some embodiments of the disclosed implant system, components such as the cage or the securing element may have components customized to be sized for specific patients and for specific uses. For example, the implant system may have a cage that is custom sized from patient data to fit that specific patient and provide specific features for that patient.

In some embodiments of the disclosed implant system, the coupling mechanism may incorporate a keyway mechanism to help move the staple heads through the different location and alignment positions. One example of a suitable keyway mechanism includes the keyway mechanism disclosed in co-pending PCT Application No. PCT/US25/45275 filed on Sep. 7, 2025, the entire contents of which are herein incorporated by reference.

Although the examples shown are asymmetrical or non-symmetrical about a horizontal mid-line plane of the implant device, it is understood that some embodiments of the implant components may be configured to create a symmetrical implant device about its mid-line horizontal plane.

Appropriate instrumentation as known to a skilled artisan would be provided to the surgeon to assist and facilitate every step of the above implantation procedure. These instruments would include but not be limited to, cutting guides, cage introducer/retractor, cage inserter/holders, sizing template, drill template, drill bits, plate holder/introducer, and screwdrivers. A skilled artisan would also adapt these instruments appropriately to accommodate the desired surgical approach; direct anterior, anterior lateral, anterior-to-psoas (ATP), oblique or direct lateral.

The Implant System Used in Intervertebral Applications

Described below in detail is an example anterior lumbar interbody fusion (ALIF) procedure which is performed from an anterior approach of the patient's spine. In this type of a procedure, placement of the vertebral implant device between the vertebral bodies is done from an anterior approach trajectory. For example, see FIGS. 7 and 12. The procedures and implant systems may be used with any lumbar vertebra of the lumbar spine, any thoracic vertebra of the thoracic spine, or any cervical vertebra of the cervical spine. In some embodiments, these procedures are particularly suitable for interbody fusion at the L5-S1 level which is the most common level of vertical foraminal stenosis.

An example method of implanting one example of the implant system consistent with the implant system of FIGS. 6A-6C generally comprises the steps described below.

Access is made to the vertebral body through an incision in the lower abdomen. The damaged disc or discs are removed between the affected vertebrae, and the site is prepared for the vertebral implant device.

The distal forked end of the implant insertion channel guide (for example only, see example at FIG. 13A) is positioned with its distal tip between the two vertebral bodies.

The staple drive handle assembly is secured to the vertebral implant device and the implant insertion channel guide and the cage is advanced and positioned between the two vertebral bodies. The outer rod of the staple drive handle assembly is positioned in the locked position during insertion. This locked position keeps the staple in the insertion position.

Prior to implanting, the cage may be filled with bone graft material of choice. During this step, the staple is in an insertion position to pass through the insertion tool and the osteotomy site with the cage. With the cage in place, the implant insertion channel guide can then be removed.

Once the vertebral implant is positioned between the vertebrae, the staple drive handle assembly is used to engage the coupling mechanism of the implant device and rotate the outer nut from stabilized position 3, the locked or stabilized position, to translate position 1, the translate position. With the outer nut moved into the translate position 1 by the outer drive rod, the inner nut may be rotated by the inner drive rod to cause the staple shaft and staple to translate relative to the cage. Once the staple is outside of the side borders of the vertebral body endplates, the outer nut can be rotated to the rotate position 2, the rotate position, by the outer drive rod. With the outer nut in the rotate position 2, the inner drive rod is rotated to rotate the inner nut, the wheel, and the staples into the deployed position. In the deployed position, the staples are positioned with tines to engage the outside surface of the vertebral body sidewalls. With the staples in the deployed position, the outer nut is rotated by the outer drive rod to the translate position 1 and the inner drive rod is rotated to translate the staples toward the cage and to draw the staples into engagement with the sidewalls of the vertebral body in their stabilized position. Once in the stabilized position, the outer drive rod is rotated to place the outer nut in the stabilized position 3 to keep the staples in the stabilized position.

The Implant System Used in Intravertebral Applications:

It is understood that the above-described implant systems and methods may also be used for intravertebral applications such as an intervertebral procedure. For example, the implant systems may be able to use the cage to separate two portions of a vertebral body that has undergone an osteotomy and the staples may be used to secure the implant device to a superior and inferior portions of the vertebral body.

Generally, these implant systems have similar features in respect to the horizontal plane so that sufficient structure is available to engage both portions of the vertebral body. These implant systems may also have retracting or extending features for the staples to further secure the implant device to the portions of the vertebral body.

The Implant System Used in Arthrodesis Applications:

As the above-described systems and devices may be configured for use in intervertebral or intravertebral applications, the implant systems may be used to fuse opposing bones in other body joints in applications such as an arthrodesis procedure.

For example, the implant system may be sized and configured so that the staples secure the implant device cage between two bones of a finger or foot/ankle joint.

Although this invention has been described in the above forms with a certain degree of particularity, it is understood that the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention which is defined in the claims and their equivalents.

We claim:

1. An orthopedic implant device comprising:

a cage having a first lateral side and a second lateral side;

a securing element;

the securing element is movable relative to the cage whereby the securing element is configured to move from an insertion position to a stabilized position;

the securing element comprises at least one staple positioned near one of the first lateral side of the cage or the second lateral side of the cage;

whereby the at least one staple is configured to be secured to a sidewall of a bone;

a coupling mechanism configured to rotate the at least one staple; and the coupling mechanism is positioned on a proximal side of the cage whereby the coupling mechanism may be manipulated from the proximal side of the cage.

2. The orthopedic implant device of claim 1 wherein:

the at least one staple is further configured to translate along an axis that is non-parallel to an approach trajectory of the orthopedic implant device.

3. The orthopedic implant device of claim 1 wherein:

the cage further comprises a top side and a bottom side;

the top side of the cage is configured to engage a first bone portion of the bone;

the bottom side of the cage is configured to engage a second bone portion of the bone;

the at least one staple comprises a first staple and a second staple;

the first staple having a first staple head positioned near the first lateral side of the cage; and the second staple having a second staple head positioned near the second lateral side of the cage.

4. The orthopedic implant device of claim 1 wherein:

the cage further comprises a top side and a bottom side;

the top side of the cage is configured to engage a first bone portion of the bone;

the bottom side of the cage is configured to engage a second bone portion of the bone;

the at least one staple comprises a first staple and a second staple;

the first staple comprises a first staple head and a first staple shaft;

the second staple comprises a second staple head and a second staple shaft; and the first staple shaft is configured to be rotated to move the first staple head and the second staple shaft is configured to be rotated to move the second staple head.

5. The orthopedic implant device of claim 1 wherein:

the at least one staple comprises a first staple and a second staple;

the first staple comprises a first staple head and a first staple shaft;

the second staple comprises a second staple head and a second staple shaft; and the first staple shaft is configured to translate to move the first staple head and the second staple shaft is configured to translate to move the second staple head.

6. The orthopedic implant device of claim 1 wherein:

the at least one staple comprises a first staple and a second staple;

the first staple has a first staple head positioned near the first lateral side of the cage;

the second staple has a second staple head positioned near the second lateral side of the cage;

the coupling mechanism is configured to be manipulated by a staple drive handle assembly from the proximal side of the cage;

the coupling mechanism is configured to move each of the first staple and the second staple;

the first staple is configured to rotate about a first staple rotation axis that is non-parallel to an approach trajectory of the orthopedic implant device; and the second staple is configured to rotate about a second staple rotation axis that is non-parallel to the approach trajectory of the orthopedic implant device.

7. The orthopedic implant device of claim 1 wherein the orthopedic implant device is configured to be positioned from one of an anterior approach trajectory, an anterior lateral approach trajectory, or an anterior oblique approach trajectory relative to a bone.

8. The orthopedic implant device of claim 1 wherein:

the at least one staple comprises a first staple and a second staple;

one of the first staple or the second staple is configured to rotate about a staple rotation axis; and the coupling mechanism is configured to be movable by a rotation about a coupling mechanism rotation axis that is aligned in a non-parallel orientation to the staple rotation axis of one of the first staple or the second staple.

9. The orthopedic implant device of claim 1 wherein:

the orthopedic implant device is configured as an implant device for a vertebra; and the orthopedic implant device is configured to be used in one or an anterior lumbar interbody fusion (ALIF) procedure or an anterior lumbar intrabody fusion (ALIF) procedure.

10. The orthopedic implant device of claim 1 wherein:

the orthopedic implant device is configured as an implant device for a vertebra; and the vertebra comprises a first (S1) vertebra of a sacral spine.

11. The orthopedic implant device of claim 1 wherein:
the at least one staple comprises a first staple and a second staple; and
the orthopedic implant device is configured as an implant device for a vertebra;
the vertebra comprises a first vertebra and a second vertebra;
the first vertebra comprises an S1 vertebra of a sacral spine; and
the second vertebra comprises an L5 vertebra of a lumbar spine whereby the first staple and the second staple are configured to secure the orthopedic implant device to a sidewall of the L5 vertebra and a sidewall of the S1 vertebra.

12. The orthopedic implant device of claim 1 wherein:
the at least one staple comprises a first staple and a second staple; and
the first staple and the second staple each have a staple head positioned outside of an outer wall of the cage.

13. The orthopedic implant device of claim 1 wherein:
at least one staple comprises a first staple and a second staple; and
the first staple and the second staple each have a staple head positioned within an outer wall of the cage.

14. The orthopedic implant device of claim 1 wherein:
the at least one staple comprises a first staple and a second staple;
the cage comprises a middle section, a first lateral section and a second lateral section;
the first lateral section and the second lateral section are each moveable relative to the middle section;
the first lateral section is configured to move with the first staple when the first staple moves from the insertion position to an extended position; and
the second lateral section is configured to move with the second staple when the second staple moves from the insertion position to an extended position.

15. The orthopedic implant device of claim 1 wherein a portion of the cage comprises a lattice surface configuration.

16. An orthopedic implant device comprising:
a cage having a longitudinal axis extending from a proximal side to a distal side;
the cage having a transverse axis extending from a first lateral side to a second lateral side;
one or more staple each having a staple head;
a coupling mechanism configured to rotate the one or more staple about a staple rotation axis of the one or more staple;
the one or more staple and the cage operably coupled whereby the one or more staple head is positioned near to one of the first lateral side of the cage or the second lateral side of the cage;
whereby the one or more staple head is configured to be secured to a first bone portion and a second bone portion; and
the coupling mechanism is configured to rotate about a coupling mechanism rotation axis that is aligned in a non-parallel orientation to the staple rotation axis of the one or more staple.

17. The orthopedic implant device of claim 16 wherein the one or more staple is configured to move from a deployed position to a stabilized position.

18. The orthopedic implant device of claim 16 wherein the one or more staple head is positioned outside of an outer wall of the cage.

19. The orthopedic implant device of claim 16 wherein the one or more staple head is positioned inside of an outer wall of the cage.

20. The orthopedic implant device of claim 16 wherein:
the one or more staple head is positioned near to one of the first lateral side of the cage or the second lateral side of the cage; and
the coupling mechanism is positioned on a proximal side of the cage whereby the coupling mechanism may be manipulated by a staple drive handle assembly from the proximal side of the cage.

21. The orthopedic implant device of claim 16 wherein the one or more staple comprises a first staple and a second staple.

22. A method to secure an orthopedic implant device to a first bone portion and a second bone portion, the method comprising:
providing an orthopedic implant device comprising:
a cage having a longitudinal axis extending from a proximal side to a distal side,
the cage having a transverse axis extending from a first lateral side to a second lateral side,
one or more staple each having a staple head,
a coupling mechanism configured to rotate the one or more staple about a staple rotation axis of the one or more staple,
the one or more staple and the cage operably coupled whereby the one or more staple head is positioned near to one of the first lateral side of the cage or the second lateral side of the cage,
whereby the one or more staple head is configured to be secured to a first bone portion and a second bone portion, and
the coupling mechanism is configured to rotate about a coupling mechanism rotation axis that is aligned in a non-parallel orientation to the staple rotation axis of the one or more staple;
positioning the cage into an opening between the first bone portion and the second bone portion; and
moving one of the one or more staple to secure the cage to the first bone portion and the second bone portion.

23. The method of claim 22 wherein the step of positioning the cage into the opening between the first bone portion and the second bone portion comprises positioning, from an anterior position to the cage, the cage into the opening between the first bone portion and the second bone portion.

24. The method of claim 22 wherein:
the one or more staple is moved by a coupling mechanism; and
the step of moving one of the one or more staple to secure the cage to the first bone portion and the second bone portion comprises:
engaging the coupling mechanism to move the one or more staple from an insertion position to a deployed position, and
engaging the coupling mechanism to move the one or more staple from the deployed position to a stabilized position whereby the cage is secured to the first bone portion and the second bone portion.

25. The method of claim 24 wherein:
the step of engaging the coupling mechanism to move the one or more staple from an insertion position to a deployed position comprises rotating the coupling mechanism about a coupling mechanism rotation axis whereby the one or more staple rotates about a staple rotation axis to move the one or more staple from the insertion position to the deployed position; and the coupling mechanism rotation axis is non-parallel to the staple rotation axis.

26. The method of claim 24 wherein:

the step of engaging the coupling mechanism to move the one or more staple from the deployed position to a stabilized position comprises rotating the coupling mechanism about a coupling mechanism rotation axis whereby the one or more staple translates along a staple rotation axis to move the one or more staple from the deployed position to the stabilized position; and the coupling mechanism rotation axis is non-parallel to the staple rotation axis.

27. An orthopedic implant device comprising:

a cage;

a securing element;

the securing element is configured to rotate about a securing element rotation axis;

a coupling mechanism configured to move the securing element; and the coupling mechanism is configured to be movable by a rotation about a coupling mechanism rotation axis that is aligned in a non-parallel orientation to the securing element rotation axis.

28. The orthopedic implant device of claim 27 wherein:

the securing element comprises a first staple and a second staple;

the securing element rotation axis comprises a staple rotation axis of at least one of the first staple and the second staple;

the coupling mechanism is configured to move at least one of the first staple and the second staple; and the coupling mechanism rotation axis is aligned in a non-parallel orientation to the staple rotation axis of at least one of the first staple and the second staple.

29. The orthopedic implant device of claim 27 wherein the coupling mechanism is positioned on a proximal side of the cage whereby the coupling mechanism may be manipulated from the proximal side of the cage.

30. The orthopedic implant device of claim 27 wherein:

the securing element comprises a first staple and a second staple;

the first staple has a first staple head positioned near a first lateral side of the cage; and the second staple has a second staple head positioned near a second lateral side of the cage.

31. The orthopedic implant device of claim 27 wherein:

the securing element comprises a first staple and a second staple; and the first staple and the second staple each have a staple head positioned outside of an outer wall of the cage.

32. The orthopedic implant device of claim 27 wherein:

the securing element comprises a first staple and a second staple; and the first staple and the second staple each have a staple head positioned within an outer wall of the cage.

* * * * *